United States Patent [19]

Pitteloud

[11] Patent Number: 5,777,008

[45] Date of Patent: Jul. 7, 1998

[54] OLIGOMERIC HALS PHOSPHITES AND HALS PHOSPHONITES AS STABILISERS

[75] Inventor: Rita Pitteloud, Praroman, Switzerland

[73] Assignee: Ciba Specialty Chemicals Corporation, Tarrytown, N.Y.

[21] Appl. No.: 451,114

[22] Filed: May 25, 1995

[30] Foreign Application Priority Data

Jun. 2, 1994 [CH] Switzerland ............ 01734/94-8

[51] Int. Cl.$^6$ ............ C08K 5/3435; C08K 5/5353
[52] U.S. Cl. ............ 524/103; 524/102; 546/14; 546/22; 546/24; 546/192; 546/208; 546/223; 546/242; 546/244
[58] Field of Search ............ 252/400.24; 524/102, 524/103, 108; 546/223, 224, 190, 192, 242, 244, 208, 14, 22, 24

[56] References Cited

U.S. PATENT DOCUMENTS

| | | | |
|---|---|---|---|
| 3,904,581 | 9/1975 | Murayama et al. | 260/45.8 |
| 3,974,127 | 8/1976 | Tanikella et al. | 260/75 |
| 4,096,114 | 6/1978 | Minagawa et al. | 260/45.8 |
| 4,141,883 | 2/1979 | Soma et al. | 260/45.8 |
| 4,210,576 | 7/1980 | Di Battista et al. | 260/45.8 |
| 4,279,804 | 7/1981 | Cantatore et al. | 260/45.8 |
| 4,396,769 | 8/1983 | Ferreira et al. | 546/188 |
| 4,798,836 | 1/1989 | Minagawa et al. | 524/89 |
| 4,883,870 | 11/1989 | Cantatore et al. | 540/598 |
| 5,187,275 | 2/1993 | Borzatta et al. | 544/207 |
| 5,198,546 | 3/1993 | Borzatta et al. | 544/198 |
| 5,239,076 | 8/1993 | Meier et al. | 546/187 |
| 5,340,855 | 8/1994 | Meier et al. | 524/102 |
| 5,405,891 | 4/1995 | Pitteloud | 524/102 |

FOREIGN PATENT DOCUMENTS

| | | | |
|---|---|---|---|
| 0302020 | 2/1989 | European Pat. Off. | C07D 211/58 |
| 0314472 | 5/1989 | European Pat. Off. | C07D 401/14 |
| 0336895 | 10/1989 | European Pat. Off. | C07D 211/58 |
| 0356688 | 3/1990 | European Pat. Off. | |
| 2380290 | 9/1978 | France | |
| 3928291 | 2/1991 | Germany | |
| 4306747 | 9/1993 | Germany | |
| 57-21368 | 2/1982 | Japan | |
| 2247241 | 2/1992 | United Kingdom | |
| 9533003 | 12/1995 | WIPO | C08K 5/00 |

OTHER PUBLICATIONS

R. Gächter/H. Müller (Ed.), Plastics Handbook 3rd Ed., p. 47, Hanser, München (1990).
T. König et al., J. Prakt. Chem. 334, 333–349 (1992) (abstract only).
R.A. Bartlett et al., J. Amer. Chem. Soc. 109, 5699 (1987).
Organic Syntheses, Coll. vol. IV, 784–785 (1963).
Th. Weil et al., Helv. Chim. Acta 1952, 1412 (no translation).
F. Nief et al., Tetrahedron 47 (33), 6673 (1991).
Ullmanns Enzyklopädie Der Technischen Chemie, Bd. 13, Seiten 85–94 (Verlag Chemie, Weinheim, 1977, (no translation).
F. Richter, Beilstein EII, vol. 22, Seite 321 (1953) (no translation).
Derw Abstract 93–296322 (38) of DE 4306747 (1993).
Derw Abstract 91–066407 (10) of DE 3928291 (1991).

*Primary Examiner*—Cynthia Harris
*Assistant Examiner*—Deanna Baxam
*Attorney, Agent, or Firm*—Luther A. R. Hall; Victoria M. Malia; Michele Kovaleski

[57] ABSTRACT

Novel oligomeric compounds of formula I

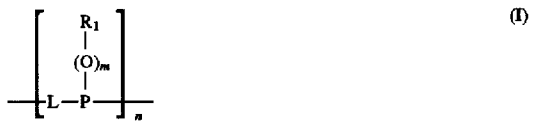

wherein the general symbols are as defined in claim 1, are disclosed as stabilisers for protecting organic material against oxidative, thermal or light-induced degradation.

8 Claims, No Drawings

OLIGOMERIC HALS PHOSPHITES AND HALS PHOSPHONITES AS STABILISERS

The present invention relates to novel oligomeric HALS phosphites and HALS phosphonites, to compositions comprising an organic material, preferably a polymer, and said novel oligomeric HALS phosphites and HALS phosphonites, as well as to the use thereof for stabilising organic materials against oxidative, thermal or light-induced degradation.

Organic phosphites and phosphonites are known in the art as co-stabilisers, secondary antioxidants and processing stabilisers, inter alia for polyolefins. Examples of such known phosphite stabilisers will be found in R. G ächter/H. Müller (Ed.), Plastics Additives Handbook, 3rd Ed., p. 47, Hanser, Munich 1990, and in EP-A-356 688.

Hindered amines, including in particular compounds containing 2,2,6,6-tetramethylpiperidyl groups, preferably find utility as light stabilisers (hindered amine light stabilisers; HALS).

Phosphites and phosphonites containing HALS structural units are described, for example, by T. Konig et al, J. prakt. Chem. 334, 333–349 (1992), in U.S. Pat. No. 5 239 076, GB-A-2 247 241, DE-A-4 306 747 and FR-A-2 380 290.

There continues to be a demand for effective stabilizers for organic materials which are sensitive to oxidative, thermal and/or light-induced degradation.

It has now been found that a selected group of such HALS phosphites and HALS phosphonites is particularly suitable as stabilizers for organic materials which are sensitive to oxidative, thermal or light-induced degradation. Particular mention should be made of the suitability of said compounds as processing stabilizers for synthetic polymers.

The present invention therefore relates to oligomeric compounds of the formula I

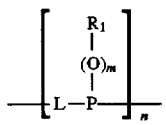

wherein L is a group of formula II or III

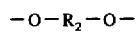

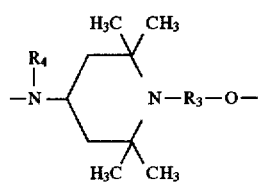

$R_1$ is $C_1$–$C_{25}$ alkyl, $C_2$–$C_{25}$alkyl which is interrupted by oxygen, sulfur or >NR—$R_5$; $C_2$–$C_{24}$-alkenyl, unsubstituted or $C_1$–$C_4$alkyl-substituted $C_5$–$C_{15}$cycloalkyl; unsubstituted or $C_1$–$C_4$-alkyl-substituted $C_5$–$C_{15}$cycloalkenyl; $C_7$–$C_9$phenylalkyl which is unsubstituted or substituted at the phenyl ring by $C_1$–$C_4$alkyl; or tetrahydroabietyl; or $R_1$ is also a radical of formula IV

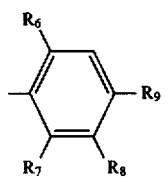

$R_2$ is a group of formula V to XVI

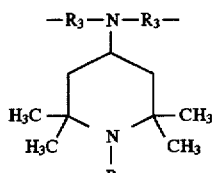

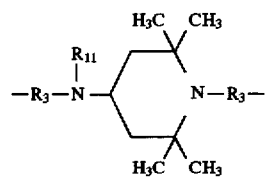

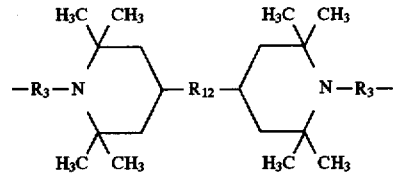

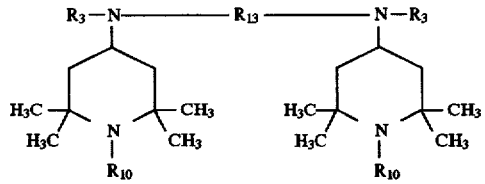

-continued
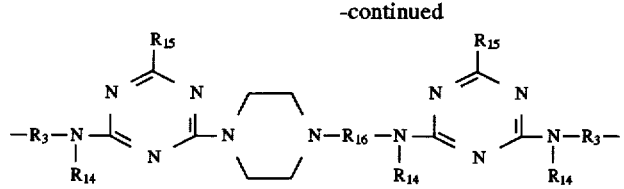 (IX)
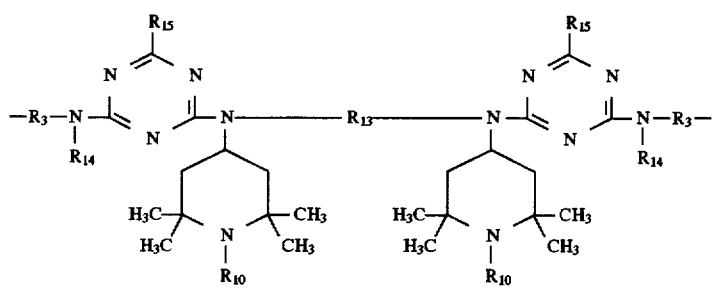 (X)
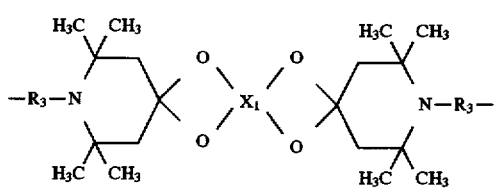 (XI)
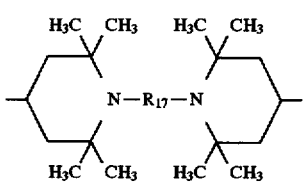 (XII)
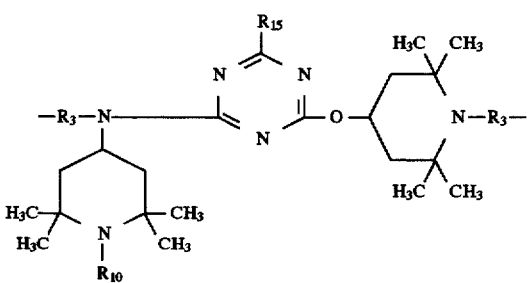 (XIII)
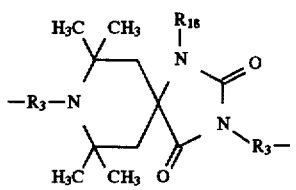 (XIV)
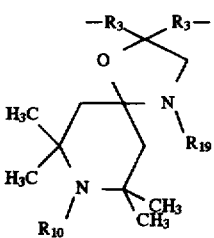 (XV)

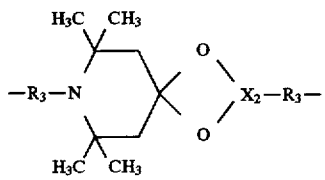
(XVI)

$R_3$ is $C_1$–$C_{18}$alkylene, $C_2$–$C_{18}$aklylene which is interrupted by oxygen, sulfur or >N—$R_5$; $C_4$–$C_8$alkenylene or phenylethylene, $R_4$ is $C_1$–$C_8$alkyl or a radical of formula XVII

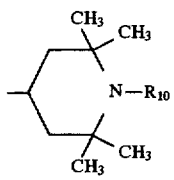
(XVII)

$R_5$ is hydrogen or $C_1$–$C_8$alkyl, $R_6$ and $R_7$ are each independently of the other hydrogen, $C_1$–$C_{25}$alkyl, $C_2$–$C_{24}$alkenyl, unsubstituted or $C_1$–$C_4$alkyl-substituted $C_5$–$C_8$cycloalkyl; unsubstituted or $C_1$–$C_4$alkyl-substituted phenyl; unsubstituted or $C_1$–$C_4$alkyl-substituted $C_5$–$C_8$cycloalkenyl; $C_7$–$C_9$phenylalkyl or —$CH_2$—S—$R_{20}$.

$R_8$ is hydrogen or methyl, $R_9$ is hydrogen, $C_1$–$C_{25}$alkyl, $C_2$–$C_{24}$alkenyl, unsubstituted or $C_1$–$C_4$alkyl-substituted $C_5$–$C_8$cycloalkyl; unsubstituted or $C_1$–$C_4$alkyl-substituted phenyl; unsubstituted or $C_1$–$C_4$-alkyl-substituted $C_5$–$C_8$cycloalkenyl; $C_7$–$C_9$phenylalkyl, —$CH_2$—S—$R_{20}$, —$(CH_2)_p COOR_{21}$ or —$(CH_2)_q OR_{22}$, $R_{10}$ is hydrogen, $C_1$–$C_8$alkyl, O', OH, NO, —$CH_2CN$, $C_1$–$C_{18}$alkoxy, $C_5$–$C_{12}$cycloalkoxy, $C_3$–$C_6$alkenyl, $C_3$–$C_6$alkynyl, $C_1$–$C_8$acyl, $C_7$–$C_9$phenylalkyl which is unsubstituted or substituted at the phenyl ring by $C_1$–$C_4$alkyl, $R_{11}$ is $C_1$–$C_8$alkyl or a radical of formula XVII

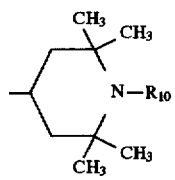
(XVII)

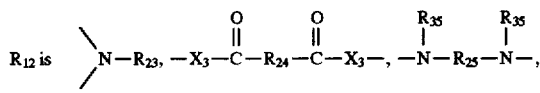

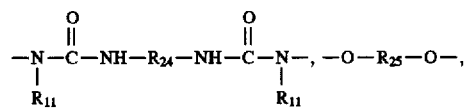

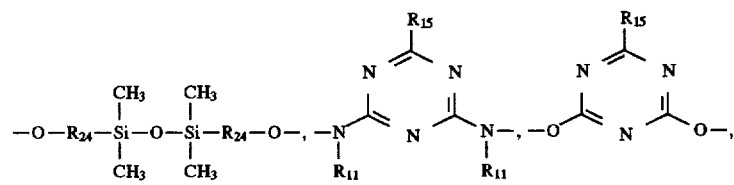

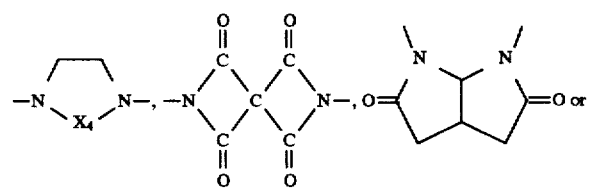

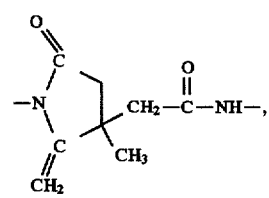

-continued

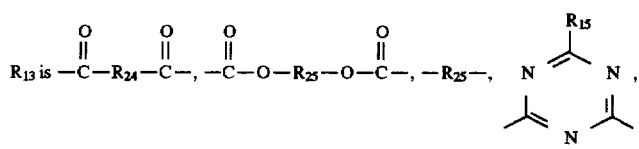

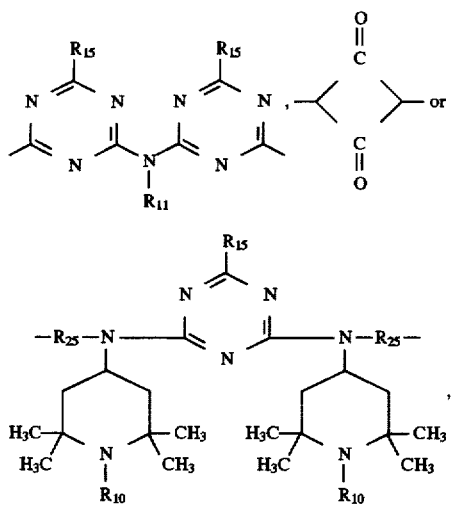

$R_{14}$ is $C_1$–$C_8$alkyl or a radical of formula XVII

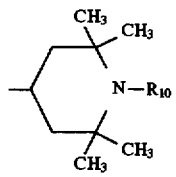
(XVII)

$R_{15}$ is —$OR_{26}$, —$NHR_{27}$,

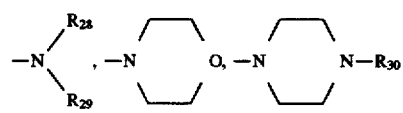

or —$SR_{26}$.

$R_{16}$ and $R_{17}$ are each independently of the other

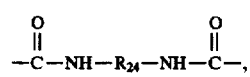

$C_1$–$C_{18}$-alkylene, $C_2$–$C_{18}$alkylene which is interrupted by oxygen, sulfur or >N—$R_5$; $C_2$–$C_{18}$alkenylene, $C_2$–$C_{18}$alkynylene, $C_2$–$C_{20}$alkylidene, $C_7$–$C_{20}$phenylalkylidene, $C_5$–$C_8$cycloalkylene, $C_7$–$C_8$bicycloalkylene, unsubstituted or $C_1$–$C_4$alkyl-substituted phenylene or naphthylene;

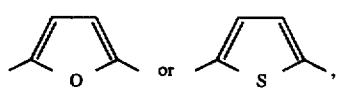

$R_{18}$ and $R_{19}$ are each independently of the other hydrogen or $C_1$–$C_8$alkyl, $R_{20}$ is $C_1$–$C_{18}$alkyl, unsubstituted or $C_1$–$C_4$alkyl-substituted $C_5$–$C_{12}$cycloalkyl; unsubstituted or $C_1$–$C_4$alkyl-substituted phenyl; $C_7$–$C_9$phenylalkyl or —$(CH_2)_r COOR_{21}$, $R_{21}$ is $C_1$–$C_{18}$alkyl, unsubstituted or $C_1$–$C_4$alkyl-substituted $C_5$–$C_{12}$cycloalkyl; unsubstituted or $C_1$–$C_4$alkyl-substituted phenyl; or $C_7$–$C_9$phenylalkyl, $R_{22}$ is $C_1$–$C_{25}$alkyl, unsubstituted or $C_1$–$C_4$alkyl-substituted phenyl; $C_7$–$C_9$phenylalkyl, $C_1$–$C_{25}$alkanoyl, $C_3$–$C_{25}$alkenoyl, $C_3$–$C_{25}$alkanoyl which is interrupted by oxygen, sulfur or >N—$R_5$; $C_6$–$C_9$cycloalkylcarbonyl, unsubstituted or $C_1$–$C_{12}$alkyl-substituted benzoyl; thenoyl or furoyl darstellt, $R_{23}$ is $C_1$–$C_8$alkyl, $R_{24}$ is a direct bond, $C_1$–$C_{18}$alkylene, $C_2$–$C_{18}$alkylene which is interrupted by oxygen, sulfur or >N—$R_5$; $C_2$–$C_{18}$alkenylene, $C_2$–$C_{20}$alkylidene, $C_7$–$C_{20}$phenylalkylidene, $C_5$–$C_8$-cycloalkylene, $C_7$–$C_8$bicycloalkylene, unsubstituted or $C_1$–$C_4$alkyl-substituted phenylene or naphthylene;

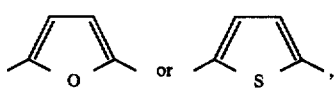

$R_{25}$ is $C_1$–$C_{18}$alkylene, $C_2$–$C_{18}$alkylene which is interrupted by oxygen, sulfur or >N—$R_5$; $C_2$–$C_{18}$alkenylene, $C_2$–$C_{20}$alkylidene, $C_7$–$C_{20}$phenylalkylidene, $C_5$–$C_8$cycloalkylene, $C_7$–$C_8$bicycloalkylene, unsubstituted or $C_1$–$C_4$alkyl-substituted phenylene or naphthylene;

$R_{26}$ is $C_1$–$C_{25}$alkyl, $C_2$–$C_{25}$alkyl which is interrupted by oxygen, sulfur or >N—$R_5$; $C_2$–$C_{24}$alkenyl, unsubstituted or $C_1$-$C_4$alkyl-substituted $C_5$-$C_{15}$cycloalkyl; unsubstituted or $C_1$-$C_4$alkyl-substituted $C_5$-$C_{15}$cycloalkenyl; $C_7$-$C_9$phenylalkyl which is unsubstituted or substituted at the phenyl ring by $C_1$-$C_4$alkyl; unsubstituted or $C_1$-$C_4$alkyl-substituted phenyl;

$R_{27}$, $R_{28}$, $R_{29}$ and $R_{30}$ are each independently of one another hydrogen, $C_1$-$C_{18}$alkyl or a radical of formula XVII

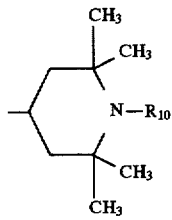

$R_{31}$ is $C_1$-$C_4$alkyl or hydroxymethyl, $R_{32}$ is hydrogen or $C_1$-$C_8$alkyl, $R_{33}$ is hydrogen, $C_1$-$C_8$alkyl or a radical of formula XVII

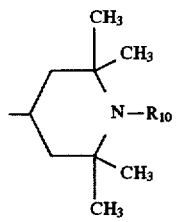

$R_{34}$ is hydrogen, $C_1$-$C_{20}$alkyl, $C_5$-$C_{12}$cycloalkyl, unsubstituted or $C_1$-$C_4$alkyl-substituted phenyl;

$R_{35}$ is $C_1$-$C_{25}$alkanoyl, unsubstituted or $C_1$-$C_4$alkyl-substituted benzoyl; or

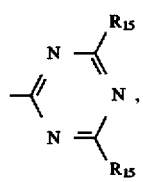

$X_1$ is a group of formula XVIII, XIX, XX or XXI

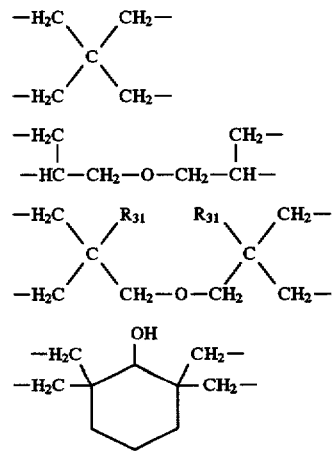

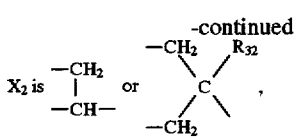

$X_3$ is oxygen or >N—$R_{33}$, $X_4$ is >C=O, >C=S or >CH—$R_{34}$, m is 0 or 1, n is an integer from 2 to 25, p is 0, 1 or 2, q is an integer from 3 to 8, and r is 1 or 2, with the proviso that in the structural repeating units of formula I the group L, the radial $R_1$, and the indices m are identical or different.

Alkyl having up to 25 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl or docosyl. One of the preferred meanings of $R_1$, $R_6$, $R_7$, $R_9$, $R_{22}$, $R_{26}$ and $R_{34}$ is, for example, $C_1$-$C_{18}$alkyl, in particular $C_1$-$C_{12}$alkyl, for example $C_1$-$C_8$-alkyl. One of the preferred meanings of $R_6$, $R_7$ und $R_9$ is, for example, $C_1$-$C_4$alkyl, in particular tert-butyl. One of the preferred meanings of $R_4$, $R_5$, $R_{10}$, $R_{11}$, $R_{14}$, $R_{18}$, $R_{19}$, $R_{23}$, $R_{32}$ and $R_{33}$ is, for example, $C_1$-$C_6$alkyl, in particular $C_1$-$C_5$alkyl, for example $C_{1-C4}$-alkyl. One of the preferred meanings of $R_{20}$, $R_{21}$, $R_{27}$, $R_{28}$, $R_{29}$ and $R_{30}$ is, for example, $C_1$-$C_{16}$alkyl, in particular $C_1$-$C_{14}$alkyl, for example $C_1$-$C_{12}$alkyl. One of the preferred meanings of $R_{27}$, $R_{28}$, $R_{29}$ and $R_{30}$ is, for example, $C_1$-$C_{12}$alkyl, in particular $C_{1-C10}$alkyl, for example $C_1$-$C_8$alkyl.

$C_2$-$C_{25}$alkyl which is interrupted by oxygen, sulfur or >NR—$R_5$ can be interrupted once or more than once and is, for example, $CH_3$—O—$CH_2$—, $CH_3$—S—$CH_2$—, $CH_3$—NH—$CH_2$—, $CH_3$—N($CH_3$)—$CH_2$—, $CH_3$—O—$CH_2CH_2$—O—$CH_2$—, $CH_3$—(O—$CH_2CH_2$—)$_2$O—$CH_2$—, $CH_3$—(O—$CH_2CH_2$—)$_3$O—$CH_2$— or $CH_3$—(O—$CH_2CH_2$—)$_4$O—$CH_2$—. One of the preferred meanings of $R_1$ und $R_{26}$ is, for example, $C_2$-$C_{18}$alkyl which is interrupted by oxygen, in particular $C_4$-$C_{18}$aLkyl which is interrupted by oxygen, for example $C_4$-$C_{12}$alkyl which is interrupted by oxygen.

Alkenyl having 2 to 24 carbon atoms is a branched or unbranched radical, for example vinyl, propenyl, 2-butenyl, 3-butenyl, isobutenyl, n-2,4-pentadienyl, 3-methyl-2-butenyl, n-2-octenyl, n-2-dodecenyl, isododecenyl, oleyl, n-2-octadecenyl or n-4-octadecenyl. One of the preferred meanings of $R_1$, $R_6$, $R_7$, $R_9$ and $R_{26}$ is alkenyl having 3 to 18, in particular 3 to 12, for example 3 to 10 carbon atoms. One of the preferred meaning of $R_{10}$ is alkenyl having 3 to 6, in particular 3 to 5, for example 3 to 4 carbon atoms.

Unsubstituted or $C_1$-$C_4$alkyl-substituted $C_5$-$C_{15}$cycloalkyl, in particular $C_5$-$C_{12}$cycloalkyl, which preferably contains 1 to 3, in particular 1 or 2, branched or unbranched alkyl radicals, is, for example, cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl, cyclooctyl or cyclododecyl. Preference is given to $C_5$-$C_8$cycloalkyl, in particular cyclohexyl.

Unsubstituted or $C_1$-$C_4$alkyl-substituted $C_5$-$C_{15}$cycloalkenyl, which preferably contains 1 to 3, in particular 1 or 2, branched or unbranched alkyl radicals, is, for example, cyclopentenyl, methylcyclopentenyl, dimethylcyclopentenyl, cyclohexenyl, methylcyclohexenyl, dimethylcyclohexenyl, trimethylcyclohexenyl, tert-butylcyclohexenyl, cycloheptenyl, cyclooctenyl or cyclododecenyl. Preference is given to $C_5$-$C_{12}$cycloalkenyl, in particular $C_5$-$C_8$cycloalkenyl, for example cyclohexenyl.

$C_7$-$C_9$phenylalkyl which is unsubstituted or substituted on the phenyl radical by $C_1$-$C_4$-alkyl and which preferably contains 1 to 3, in particular 1 or 2, branched or unbranched alkyl radicals is, for example, benzyl, α-methylbenzyl, α,α-dimethylbenzyl, 2-phenylethyl, 2-methylbenzyl, 3-methylbenzyl, 4-methylbenzyl, 2,4-dimethylbenzyl, 2,6-dimethylbenzyl or 4-tert-butylbenzyl. Benzyl is preferred.

$C_1$-$C_{18}$alkylene is a branched or unbranched radical, for example methylene, ethylene, propylene, tetramethylene, pentamethylene, hexamethylene, heptamethylene, octamethylene, decamethylene, dodecamethylene or octadecamethylene. One of the preferred meaning of $R_3$ is, for example $C_1$-$C_{12}$alkylene, in particular $C_2$-$C_{10}$alkylene, for example $C_2$-$C_8$alkylene. A preferred meaning of $R_3$ is ethylene and propylene. One of the preferred meanings of $R_{16}$ and $R_{17}$ is for example $C_2$-$C_{14}$alkylene, in particular $C_2$-$C_{12}$alkylene, for example $C_2$-$C_8$alkylene. An especially preferred meaning of $R_{16}$ and $R_{17}$ is, for example $C_4$-$C_8$alkylene. One of the preferred meaning of $R_{24}$ is, for example, $C_1$-$C_{14}$alkylene, in particular $C_1$-$C_{12}$alkylene, for example $C_1$-$C_8$alkylene. An especially preferred meaning of $R_{25}$ is, for example, $C_2$-$C_{14}$alkylene, in particular $C_2$-$C_{12}$alkylene, for example $C_2$-$C_8$alkylene.

$C_2$-$C_{18}$alkylene which is interrupted by oxygen, sulfur or >N—$R_5$ can be interrupted once or more than once and is, for example, —$CH_2$—O—$CH_2$—, —$CH_2$—S—$CH_2$—, —$CH_2$—NH—$CH_2$—, —$CH_2$—N($CH_3$)—$CH_2$—, —$CH_2$—O—$CH_2CH_2$—O—$CH_2$—, —$CH_2$—(O—$CH_2CH_2$—)$_2$O—$CH_2$—, —$CH_2$—(O—$CH_2CH_2$—)$_3$O—$CH_2$—, —$CH_2$—(O—$CH_2CH_2$—)$_4$O—$CH_2$— or —$CH_2CH_2$—S—$CH_2CH_2$—. One of the preferred meanings of $R_3$, $R_{16}$, $R_{17}$, $R_{24}$ and $R_{25}$ is, for example, $C_2$-$C_{18}$alkylene which is interruped by oxygen, in particular $C_4$-$C_{18}$alkylene which is interrupted by oxygen, for example $C_4$-$C_{12}$alkylene which is interrupted by oxygen.

$C_4$-$C_8$alkenylene $R_3$ is, for example, 2-buten-1,4-ylene. Phenylethylene is —CH($C_6H_5$)$CH_2$—.

$C_1$-$C_4$alkyl-substituted phenyl, which preferably contains 1 to 3, in particular 1 or 2, alkyl groups, is, for example, o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

Alkoxy having up to 18 carbon atoms is a branched or unbranched radical, for example methoxy, ethoxy, propoxy, isopropoxy, n-butoxy, isobutoxy, pentoxy, isopentoxy, hexoxy, heptoxy, octoxy, decyloxy, tetradecyloxy, hexadecyloxy or octadecyloxy. One of the preferred meaning of $R_{10}$ is alkoxy having 4 to 16, in particular 6 to 12 carbon atoms.

Cycloalkoxy having 5 to 12 carbon atoms is, for example, cyclopentoxy, cyclohexoxy, cycloheptoxy, cyclooctoxy, cyclodecyloxy or cyclododecyloxy. One of the preferred meanings of $R_4$ is $C_5$-$C_8$cycloalkoxy. Particular preference is given to cyclopentoxy and cyclohexoxy.

Alkynyl having 3 to 6 carbon atoms is a branched or unbranched radical, for example propynyl (propargyl, —$CH_2$—C≡CH), 2-butynyl or 3-butynyl.

Acyl having 1 to 8 carbon atoms is, for example, formyl, acetyl, propionyl, butyryl, pentanoyl, hexanoyl, heptanoyl, octanoyl, benzoyl, acryloyl or crotonyl. Preference is given to $C_1$-$C_8$alkanoyl, $C_3$-$C_8$alkenoyl or benzoyl, in particular acetyl.

Examples of $C_2$-$C_{18}$alkenylene are vinylene, methylvinylene, octenylethylene or dodecenylethylene. One of the preferred meanings of $R_{16}$, $R_{17}$, $R_{24}$ and $R_{25}$ is $C_4$-$C_{12}$alkenylene, in particular $C_4$-$C_8$alkenylene, for example 2-butenylene-1,4.

Examples of $C_2$-$C_{18}$alkynylene are —C≡C—, 2-propynylene (—C≡C—$CH_2$—), 2-butynylene (—$CH_2$—C≡C—$CH_2$—), 2-pentynylene, 2-hexynylene, 3-hexynylene, 3-heptynylene, 2-decynylene, 4-decynylene or 8-octadecynylene. One of the preferred meanings of $R_{16}$ und $R_{17}$ is $C_2$-$C_{12}$alkynylene, in particular $C_4$-$C_8$alkynylene, for example 2-butynylene.

Alkylidene of 2 to 20 carbon atoms may typically be ethylidene, propyliden, butylidene, pentylidene, 4-methylpentylidene, heptylidene, nonylidene, tridecylidene, nonadecylidene, 1-methylethylidene, 1-ethylpropylidene or 1-ethylpentylidene. One of the preferred meanings of $R_{16}$, $R_{17}$, $R_{24}$ and $R_{25}$ is for example alkylidene of 2 to 12, in particular 2 to 8, for example 2 to 6 carbon atoms.

Phenylalkylidene of 7 to 20 carbon atoms may typically be benzylidene, 2-phenylethylidene or 1-phenyl-2-hexylidene. One of the preferred meanings of $R_{16}$, $R_{17}$, $R_{24}$ and $R_{25}$ is for example phenylalkylidene of 7 to 15, in particular 7 to 12, for example 7 to 9 carbon atoms.

$C_5$-$C_8$Cycloalkylene is a saturated hydrocarbon group having two free valences and at least one ring unit and is typically cyclopentylene, cyclohexylene, cycloheptylene or cyclooctylene. Cyclohexylene is preferred.

$C_7$-$C_8$Bicycloalkylene may be bicycloheptylene or bicyclooctylene.

Unsubstituted or $C_1$-$C_4$alkyl-substituted phenylene or naphthylene is typically 1,2-, 1,3-, 1,4-phenylene, 1,2-, 1,3-, 1,4-, 1,6-, 1,7-, 2,6- or 2,7-naphthylene. 1,4-phenylene is preferred.

Alkanoyl of up to 25 carbon atoms inclusive is a branched or unbranched radical, typically including formyl, acetyl, propionyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, eicosanoyl or docosanoyl. One of the preferred meanings of $R_{22}$ and $R_{35}$ is $C_1$-$C_{18}$alkanoyl, in particular $C_1$-$C_{12}$alkanoyl, for example $C_1$-$C_8$alkanoyl. An especially preffered meaning of $R_{35}$ is $C_1$-$C_4$alkanoyl, in particular acetyl.

Alkenoyl of 3 to 25 carbon atoms is a branched or unbranched radical, typically including propenoyl, 2-butenoyl, 3-butenoyl, isobutenoyl, n-2,4-pentadienoyl, 3-methyl-2-butenoyl, n-2-octenoyl, n-2-dodecenoyl, isododecenoyl, olcoyl, n-2-octadecenoyl or n-4-octadecenoyl. Alkenoyl of 3 to 18, preferably 3 to 12, e.g. 3 to 6, most preferably 3 to 4, carbon atoms is preferred.

$C_3$-$C_{25}$-Alkanoyl interrupted by oxygen, sulfur or >N—$R_5$ will typically be $CH_3$—O—$CH_2CO$—, $CH_3$—S—$CH_2CO$—, $CH_3$—NH—$CH_2CO$—, $CH_3$—N($CH_3$)—$CH_2CO$—, $CH_3$—O—$CH_2CH_2$—O—$CH_2CO$—, $CH_3$—(O—$CH_2CH_2$—)$_2$O—$CH_2CO$—, $CH_3$—(O—$CH_2CH_2$—)$_3$O—$CH_2CO$— or $CH_3$—(O—$CH_2CH_2$—)$_4$O—$CH_2CO$—.

$C_6$-$C_9$Cycloalkylcarbonyl is typically cyclopentylcarbonyl, cyclohexylcarbonyl, cycloheptylcarbonyl or cyclooctylcarbonyl. Cyclohexylcarbonyl is preferred.

$C_1$–$C_{12}$Alkyl-substituted benzoyl which preferably carries 1 to 3, most preferably 1 or 2, alkyl groups, is typically o-, m- or p-methylbenzoyl, 2,3-dimethylbenzoyl, 2,4-dimethylbenzoyl, 2,5-dimethylbenzoyl, 2,6-dimethylbenzoyl, 3,4-dimethylbenzoyl, 3,5-dimethylbenzoyl, 2-methyl-6-ethylbenzoyl, 4-tert-butylbenzoyl, 2-ethylbenzoyl, 2,4,6-trimethylbenzoyl, 2,6-dimethyl-4-tert-butylbenzoyl or 3,5-di-tert-butylbenzoyl. Preferred substituents are $C_1$–$C_8$alkyl, most preferably $C_1$–$C_4$alkyl.

Preference is given to the oligomeric compounds of the formula I in which $R_1$ is $C_{18}$alkyl, $C_2$–$C_{18}$alkyl which is interrupted by oxygen; $C_2$–$C_{18}$alkenyl, $C_5$–$C_{15}$-cycloalkyl, $C_5$–$C_{15}$cycloalkenyl, $C_7$–$C_9$phenylalkyl or tetrahydroabietyl; or $R_1$ is also a radical of formula IV

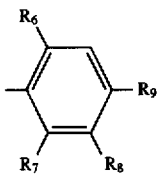

(IV)

$R_6$ and $R_7$ are each independently of the other hydrogen, $C_1$–$C_{18}$alkyl, $C_2$–$C_{18}$alkenyl, $C_5$–$C_8$cycloalkyl, phenyl, $C_5$–$C_8$cycloalkenyl, $C_7$–$C_9$phenylalkyl or —$CH_2$—S—$R_{20}$, $R_9$ is hydrogen, $C_1$–$C_{18}$alkyl, $C_2$–$C_{18}$alkenyl, $C_5$–$C_8$cycloalkyl, phenyl, $C_5$–$C_8$cycloalkenyl, $C_7$–$C_9$phenylalkyl, —$CH_2$—S—$R_{20}$, —$(CH_2)_p COOR_{21}$ or —$(CH_2)_q OR_{22}$, $R_{20}$ is $C_1$–$C_{12}$alkyl, $C_5$–$C_{12}$cycloalkyl, phenyl, $C_7$–$C_9$phenylalkyl or —$(CH_2)_r COOR_{21}$, $R_{21}$ is $C_1$–$C_{12}$alkyl, $C_5$–$C_{12}$cycloalkyl, phenyl or $C_7$–$C_9$phenylalkyl, $R_{22}$ is $C_1$–$C_{18}$alkyl, phenyl, $C_7$–$C_9$phenylalkyl, $C_1$–$C_{18}$alkanoyl, $C_3$–$C_{18}$alkenoyl, $C_3$–$C_{18}$-alkanoyl which is interrupted by oxygen; $C_6$–$C_9$cycloalkylcarbonyl, benzoyl, thenoyl or furoyl, and q is an integer from 3 to 6.

Preference is also given to the oligomeric compounds of the formula I in which $R_1$ is $C_1$–$C_{12}$alkyl, $C_3$–$C_{12}$alkenyl, cyclohexyl, benzyl or tetrahydroabietyl, or $R_1$ is also a radical of formula IV

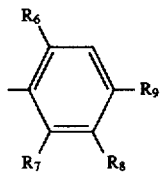

(IV)

$R_6$ and $R_7$ are each independently of the other hydrogen, $C_1$–$C_8$alkyl, cyclohexyl or phenyl, $R_9$ is hydrogen, $C_1$–$C_9$alkyl, cyclohexyl, phenyl or —$(CH_2)_p COOR_{21}$, $R_{21}$ is $C_1$–$C_{12}$alkyl or benzyl, n is an integer from 2 to 20, and p is 2.

Likewise preferred are the oligomeric compounds of the formula I in which $R_3$ is $C_1$–$C_{12}$alkylene, $C_2$–$C_{12}$alkylene which is interrupted by oxygen; $C_4$–$C_8$alkenylene or phenylethylene, $R_{11}$ is $C_1$–$C_8$alkyd),

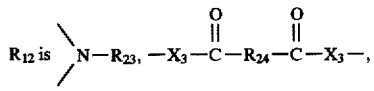

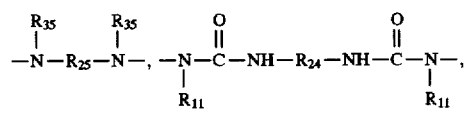

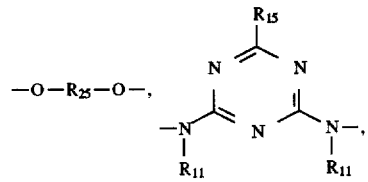

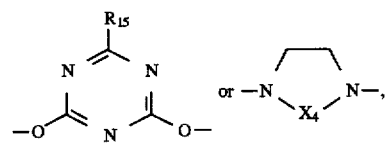

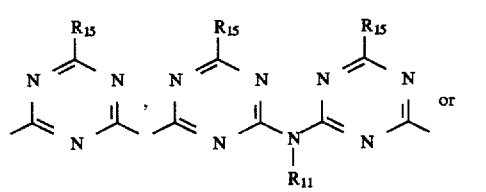

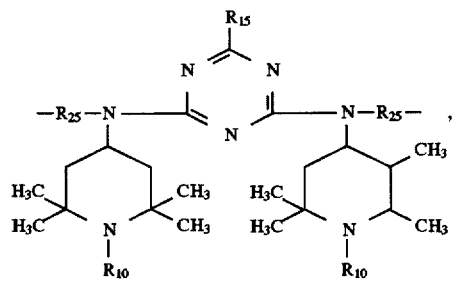

$R_{15}$ is —$OR_{26}$, —$NHR_{27}$,

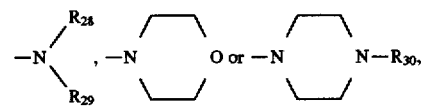

$R_{16}$ and $R_{17}$ are each independently of the other

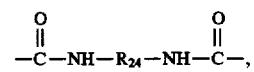

$C_2$–$C_{12}$-alkylene, $C_2$–$C_{12}$alkylene which is interrupted by oxygen; $C_2$–$C_{12}$alkenylene, $C_4$–$C_{12}$alkynylene, $C_2$–$C_{12}$alkylidene, $C_7$–$C_{12}$phenylalkylidene, $C_5$–$C_8$cycloalkylene or phenylene.

$R_{24}$ is a direct bond, $C_1$–$C_{12}$alkylene, $C_2$–$C_{12}$alkylene which is interrupted by oxygen; $C_2$–$C_{12}$alkenylene, $C_2$–$C_{12}$alkylidene, $C_7$–$C_{12}$phenylalkylidene, $C_5$–$C_8$cycloalkylene or phenylene, $R_{25}$ is $C_1$-$C_{12}$alkylene, $C_2$-$C_{12}$alkylene which is interrupted by oxygen; $C_2$-$C_{12}$akenylene, $C_2$-$C_{12}$aylidene, $C_7$-$C_{12}$phenylalkylidene, $C_5$-$C_9$cycloalkylene or phenylene, $R_{26}$ is $C_1$-$C_{18}$alkyl, $C_2$-$C_{18}$alkyl which is interrupted by oxygen; $C_2$-$C_{18}$alkenyl, $C_5$-$C_{15}$cycloalkyl, $C_5$-$C_{15}$cycloalkenyl, $C_7$-$C_9$phenylalkyl or phenyl, $R_{27}$, $R_{28}$, $R_{29}$ and $R_{30}$ are each independently of one another hydrogen, $C_1$-$C_{12}$alkyl or a radical of formula XVII

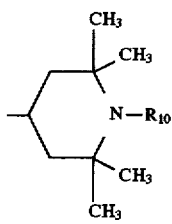 (XVII)

$R_{32}$ is hydrogen or $C_1$-$C_4$alkyl, $R_{33}$ is hydrogen or $C_1$-$C_8$alkyl, $R_{34}$ is hydrogen, $C_1$-$C_{12}$alkyl, $C_5$-$C_{12}$cycloalkyl or phenyl, $R_{35}$ is $C_1$-$C_8$alkanoyl, benzoyl or

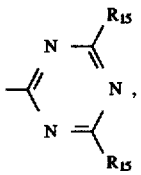

$X_1$ is a group of formula XVIII or XIX

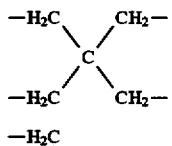 (XVIII)

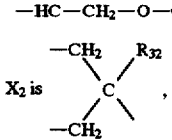 (XIX)

$X_2$ is

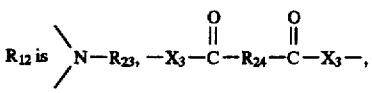

$X_4$ is >C=O or >CH—$R_{34}$, and n is an integer from 2 to 20.

Particular preference is given to the oligomeric compounds of the formula I in which $R_3$ is $C_1$-$C_8$alkylene, $C_2$-$C_8$alkylene which is interrupted by oxygen; or $C_4$-$C_8$alkenylene, $R_{11}$, is $C_1$-$C_6$alkyl, $R_{12}$ is

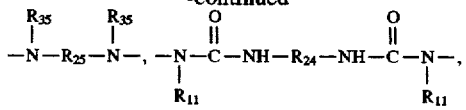

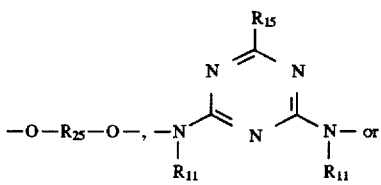

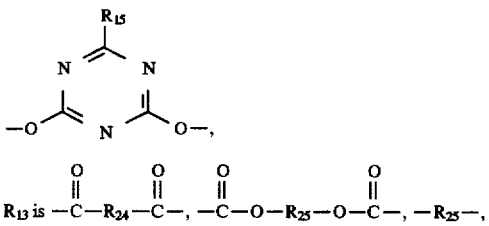

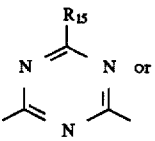

$R_{13}$ is

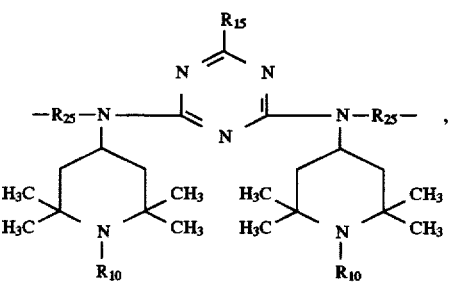

$R_{15}$ is —$OR_{26}$, —$NHR_{27}$,

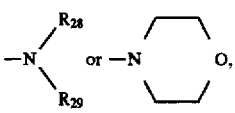

$R_{16}$ and $R_{17}$ are each independently of the other

$C_2$-$C_8$-alkylene, $C_4$-$C_{12}$alkynylene or $C_2$-$C_8$alkylidene, $R_{23}$ is $C_1$-$C_6$alkyl, $R_{24}$ is a direct bond, $C_1$-$C_{12}$alkylene, $C_2$-$C_{12}$alkylene which is interrupted by oxygen; $C_2$-$C_8$alkenylene or $C_2$-$C_8$alkylidene, $R_{25}$ is $C_2$-$C_{12}$alkylene, $C_2$-$C_{12}$alkylene which is interrupted by oxygen; $C_2$-$C_{12}$alkenylene or $C_2$-$C_{12}$alkylidene, $R_{26}$ is $C_1$-$C_{12}$alkyl, $C_2$-$C_{12}$alkenyl, cyclohexyl, benzyl or phenyl, $R_{27}$, $R_{28}$ and $R_{29}$ are each independently of one another $C_1$-$C_{10}$alkyl or a radical of formula XVII (XVII)

[structure: 2,2,6,6-tetramethylpiperidine with N—R₁₀]

R₃₂ is hydrogen or C₁–C₄alkyl,

R₃₃ is hydrogen or C₁–C₈alkyl,

R₃₄ is hydrogen or C₁–C₈alkyl,

R₃₅ is C₁–C₁₂alkanoyl, benzoyl or

[triazine structure with R₁₅ groups]

X₁ is a group of formula XVIII or XIX $$-H_2C\diagdown C \diagup CH_2-$$
$$-H_2C\diagup \phantom{C} \diagdown CH_2-$$
(XVIII)

$$-H_2C\phantom{-CH_2-O-CH_2-}CH_2-$$
$$-HC-CH_2-O-CH_2-CH-$$
(XIX)

X₂ is 
$$-CH_2\diagdown \phantom{C} \diagup R_{32}$$
$$\phantom{-CH_2\diagdown} C$$
$$-CH_2\diagup \phantom{C} \diagdown$$
, X₄ is >C=O or >CH—R₃₄, and n is an integer from 2 to 15.

Of particular interest are the oligomeric compounds of the formula I in which

R₁₀ is hydrogen, C₁–C₄alkyl, C₄–C₆alkoxy, C₅–C₈cycloalkoxy, allyl, propargyl, acetyl or benzyl.

Of specific interest are the oligomeric compounds of the formula I in which

R₁ is a radical of formula IV

[benzene ring with R₆, R₇, R₈, R₉ substituents] (IV)

R₂ is a group of formula V, VI, VII, VIII, XI, XII or XVI

[piperidine structure] (V)

-continued

[structure VI]  (VI)

[structure VII]  (VII)

[structure VIII]  (VIII)

[structure XI]  (XI)

[structure XII]  (XII)

[structure XVI]  (XVI)

R₃ is methylene or ethylene,

R₄ is C₁–C₈alkyl,

R₆ and R₇ are each independently of the other hydrogen or C₁–C₄alkyl,

R₈ is hydrogen,

R₉ is hydrogen or C₁–C₄alkyl,

R₁₀ is hydrogen or C₁–C₄alkyl, $$R_{12} \text{ is } \diagdown N-R_{23}, -X_3-\overset{O}{\underset{\|}{C}}-R_{24}-\overset{O}{\underset{\|}{C}}-X_3-,$$

[triazine/amine structures with R₁₁, R₁₅, R₂₅, R₃₅]

-continued

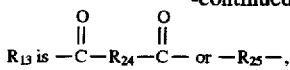

$R_{15}$ is —$OR_{26}$ or

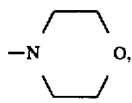

$R_{17}$ is

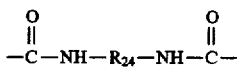

or $C_4$-$C_6$alkynylene, $R_{23}$ is $C_1$-$C_4$alkyl, $R_{24}$ is $C_2$-$C_8$alkylene, $R_{25}$ is $C_2$-$C_8$alkylene, $R_{26}$ is $C_1$-$C_4$alkyl, $R_{32}$ is hydrogen or $C_1$-$C_4$alkyl, $R_{33}$ is hydrogen or $C_1$-$C_4$alkyl, $R_{35}$ is $C_1$-$C_4$alkanoyl, $X_1$ is a group of formula XVIII

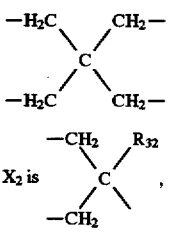

(XVIII)

$X_3$ is oxygen or >N—$R_{33}$, and n is an integer from 2 to 10.

The novel oligomeric compounds of the formula I can be prepared in a manner known per se.

The invention furthermore relates to a preferred process for the preparation of oligomeric compounds of the formula I, which comprises reacting a compound of formula XXII or a mixture of compounds of formula XXII

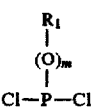

(XXII)

wherein the general symbols are as defined above, with a compound of formula XXIII or a mixture of compounds of formula XXIII

(XXIII)

wherein L is as defined above.

The reaction is carried out in the melt or in the presence of a suitable organic, polar or apolar, aprotic solvent. This reaction is preferably carried out in the presence of a base at temperatures between −20° C. and the boiling point of the solvent, in particular at temperatures between 20° and 150° C.

Bases such as amines can simultaneously also be used as solvent.

The base can be employed in various amounts, from catalytic via stoichiometric amounts up to an excess of several times the molar amount with respect to the compounds of the formula XXII or compounds of the formula XXIII employed. The hydrogen chloride formed during the reaction is, if appropriate, converted through the base into chloride, which can be removed by filtration and/or washing with a suitable aqueous or solid phase; a second, water-immiscible solvent can also be employed here. The products are expediently isolated by evaporating the organic phase and drying the residue.

Suitable solvents for carrying out the reaction include hydrocarbons (for example mesitylene, toluene, xylene, hexane, pentane or other petroleum ether fractions), halogenated hydrocarbons (for example di- or trichloromethane, 1,2-dichloroethane, 1,1,1-trichloroethane or chlorobenzene), ethers (for example diethyl ether, dibutyl ether or tetrahydrofuran), ketones (for example acetone, ethyl methyl ketone, diethyl ketone, methyl propyl ketone or cyclohexanone), furthermore acetonitrile, butyl acetate, dimethyl formamide, dimethyl sulfoxide or N-methylpyrrolidone.

Suitable bases include primary, secondary and in particular tertiary amines (for example trimethylamine, triethylamine, tributylamine, N,N-dimethylaniline, N,N-diethylaniline or pyridine), hydrides (for example lithium hydride, sodium hydride or potassium hydride) or alkoxides (for example sodium methoxide).

If hydrides (for example sodium hydride, sodium borohydride or lithium aluminium hydride), alkali metals, alkali metal hydroxides or sodium methoxide are used as bases, the corresponding alkoxide of the compound of the formula XXIII can first be formed; any reaction product formed (for example water or methanol) is removed by distillation (for example as an azeotrope with toluene) before the reaction with the compound of the formula XXII.

The structural composition of the oligomeric compounds of the formula I depends on the reaction conditions, for example the solvent or the reaction temperature, and the molar mixing ratio and the concentration of the compounds of the formulae XXII and XXIII.

Both the compound of the formula XXII and the compound of the formula XXIII can be used in a molar excess. However, it is preferred to use the HALS-diol of the formula XXIII in excess. Preferred molar mixing ratios between the compounds of the formulae XXII and XXIII are from 1.9:1 to 1:1.9, particularly preferably 1.05:1 to 1:1.8, in particular from 1:1.1 to 1:1.3.

The present invention therefore also relates to oligomeric products obtainable by reacting a compound of the formula XXII or a mixture of compounds of the formula XXII with a compound of the formula XXIII or a mixture of compounds of the formula XXIII.

The preparation of the compounds of the formulae XXII and XXIII is known.

The compounds of the formula XXII in which m=1 are known or can be prepared by processes known per se, as described, for example, in DE-A-3 928 291 or by R. A. Bartlett et al, J. Amer. Chem. Soc. 109 (19), 5699 (1987).

The compounds of the formula XXII in which m=0 are likewise known or can be prepared by processes known per se, as described, for example, in Org. Syntheses Coll. Vol. IV, 784 (1963) and by T. Weil et al., Helv. Chim. Acta 1952, 1412, or F. Nief et al., Tetrahedron 47 (33), 6673 (1991).

The compounds of the formula XXII required for the preparation of the novel compounds of the formula I can be prepared in situ analogously to the abovementioned literature procedures, and reacted further, without isolation, with a compound of the formula XXIII to give the compounds of the formula I.

The HALS compounds of the formula XXIII are known or can be prepared by processes known per se, as described, for example, in U.S. Pat. No. 3 974 127, U.S. Pat. No. 4 279 804, U.S. Pat. No. 4 798 836, U.S. Pat. No. 4 883 870 or U.S. Pat. No. 5 198 546.

L can have identical or different meanings in the recurring structural units of the formula I.

If the HALS compound of the formula XXIII is used in excess, the terminal groups of the oligomeric compounds of the formula I are, as shown in the formula XXIV

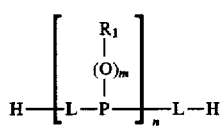 (XXIV)

predominantly hydroxyl groups or amine groups, which, if desired, can easily be derivatized by known methods. For example, these terminal groups can be esterified by means of acid halides, for example carboxylic acid halides or phosphoric acid halides, or acid anhydrides; silylated using silyl halides; alkylated or benzylated using alkyl or benzyl halides; reacted with isocyanates to give the urethanes; reacted with isothiocyanates to give the thiourethanes; reacted with sulfonyl halides and, for example, thionyl chloride to give the halides; or reacted with chlorophosphites, for example of the formula XXV, XXVI or XXVII

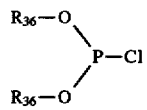 (XXV)

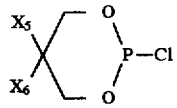 (XXVI)

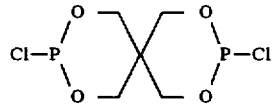 (XXVII)

in which $R_{36}$ is, for example, $C_1$–$C_{25}$alkyl, unsubstituted or $C_1$–$C_4$alkyl-substituted phenyl; or $C_7$–$C_9$phenylalkyl, and $X_5$ and $X_6$, independently of one another, are hydrogen or $C_1$–$C_4$alkyl or, together with the carbon atom to which they are bonded, form a 3,4-dehydrocyclohexylidene ring.

$C_1$–$C_4$alkyl-substituted phenyl, which preferably contains 1 to 3, in particular 1 or 2, alkyl groups, is, for example, o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

If the compound of the formula XXII is used in excess, the terminal groups of the

oligomeric compounds of the formula I in some cases also carry reactive groups, as shown in the formulae XXVIII, XXIX and XXX

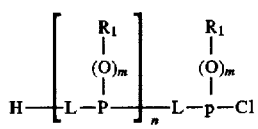 (XXVIII)

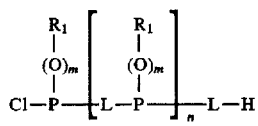 (XXIX)

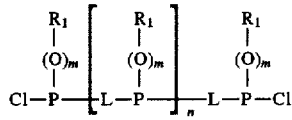 (XXX)

The chlorine atoms can be substituted by additional nucleophiles, for example phenols, alcohols, amines, mercaptans or dialkyl phosphites, by known methods with elimination of hydrochloric acid. Suitable alcohols are $C_1$–$C_8$alkanols, for example methanol, ethanol, n-propanol or n-butanol.

The oligomeric compounds of the formula I can also be in the form of ring systems of the formula XXXI

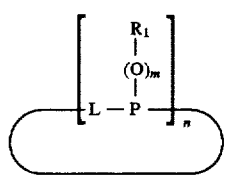 (XXXI)

in which the hydroxyl terminal group or the amine terminal group, respectively, in L cyclizes with the other chain end

with elimination of hydrochloric acid.

The present invention preferably relates to oligomeric compounds of the formula XXXII

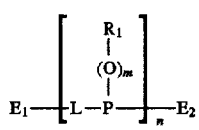 (XXXII)

in which the terminal group $E_1$ is hydrogen,

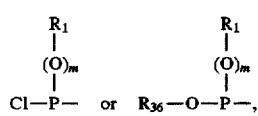

the terminal group $E_2$ is —L—H,

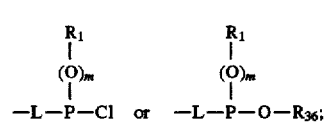

or furthermore the terminal groups $E_1$ and $E_2$ together form a direct bond (cyclic compounds); and $R_{36}$ is $C_1$–$C_8$alkyl.

Particular preference is given to oligomeric compounds of the formula XXXII in which the terminal group $E_1$ is hydrogen and the terminal group $E_2$ is a radical of the formula —L—OH, in which L is as defined above.

The novel compounds of the formula I are suitable for the stabilization of organic materials against oxidative, thermal or light-induced degradation.

Examples of such materials are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either $\pi$- or $\sigma$-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly((x-methylstyrene).

6. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/ styrene.

7. Graft copolymers of styrene or ($\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/ butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Potyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenouformaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

The invention therefore furthermore relates to compositions comprising (a) an organic material subjected to oxidative, thermal or light-induced degradation and (b) at least one oligomeric compound of the formula I or at least one oligomeric product obtainable by reacting a compound of the formula XXII or a mixture of compounds of the formula XXII with a compound of the formula XXIII or a mixture of compounds of the formula XXIII.

The organic materials to be protected are preferably natural, semisynthetic or preferably synthetic organic materials. Particular preference is given to thermoplastic polymers, in particular PVC or polyolefins, in particular polyethylene and polypropylene.

Particular emphasis should be placed on the action of the novel compounds against thermal and oxidative degradation, in particular on heating, as occurs in the processing of thermoplastics. The novel compounds are therefore highly suitable for use as processing stabilizers.

The oligomeric compounds of the formula I are preferably added to the material to be stabilized in amounts of from 0.01 to 10%, for example from 0.01 to 5%, preferably from 0.025 to 3%, in particular from 0.025 to 1%, based on the weight of the organic material to be stabilized.

In addition to the oligomeric compounds of the formula I, the novel compositions can contain further costabilizers, for example the following:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(ox-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl) phenol, 2,4-dimethyl-6-(1'-methylheptadec-1'-yl)phenol, 2,4-dimethyl-6-(1'-methyltridec-1'-yl)phenol and mixtures thereof.

1.2. Alkvlthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-do-decylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tertbutylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis-(6-tert-butyl-2-methylphenol), 4,4'-thiobis-(3,6-di-sec-amylphenol), 4,4'-bis-(2,6-dimethyl-4-hydroxyphenyl) disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methyl-cyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmer-captobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)-amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis-[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-di-methylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzyl-phosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or poly-hydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]-octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo-[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl) trimethylenediamine, N,N'-bis(3,5-di-tert-butyl-4-hydroxyphenylpropionyl)hydrazine.

1.18. Ascorbic acid (vitamin C)

1. 19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p- phenylenediamnine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)-diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylamino-phenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino) propane, (o-tolyl)biguanide, Bis[4-(1',3'-dimethylbutyl) phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohex-yldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazin, N,N,N',N'-tetraphenyl-1,4-diaminobut-2-ene, N,N-bis(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-of.

2. UV Absorbers and Light Stabilisers 2.1.2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl) phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyl-oxycarbonylethyl)phenyl) benzotriazole, 2-(3'-tert-butyl-5'-[2-(2-ethylhexyloxy) carbonyl-ethyl]-2'-hydroxyphenyl)benzotriazole, 2-(3'-dodecyl-2'-hydroxy-5'-methylphenyl)benzo-triazole, and 2-(3'-tert-butyl-2'-hydroxy-5'-(2-isooctyloxycarbonylethyl) phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl-]-2H-benzotriazole with polyethylene glycol 300; [R—CH$_2$CH$_2$—COO(CH$_2$)$_3$ ]$_2$, where R=3'-tert-butyl-4'-hydroxy-5'-2H-benzotriazol-2-ylphenyl.

2.2.2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis (4-tert-butylbenzoyl) resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxy-benzoate.

2.4. Acrylates, for example ethyl α-cyano-β,β-diphenylacrylate, isooctyl α-cyano-β, β-di-phenylacrylate, methyl α-carbomethoxycinnamate, methyl α-cyano-β-methyl-p-methoxycinnamate, butylα-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetra-methylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3, 5-di-tert-butyl-4-hydr(oxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1, 2,3,4-butane-tetracarboxylate, 1,1'-(1,2-ethane-diyl)bis(3,3, 5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2, 4-dion, bis(1-octyloxy-2,2,6,6-tetramethylpiperidyl) sebacate, bis(1-octyloxy-2,2,6,6-tetramethylpiperidyl) succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis (4-n-butylamino-2,2,6,6-tetramethylpiperidyl )-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropyl-amino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2, 5-dione, 3-dodecyl-1-(1,2,2,6,6-pentamethyl-4-piperidyl) pyrrolidine-2,5-dione, a mixture of 4-hexadecyloxy- and 4-stearyloxy-2,2,6,6-tetramethylpiperidine, a condensation product of N,N'-bis-(2,2,6,6-tetramethyl-4-piperidyl) hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro[4,5]decane, a reaction product of 7,7,9,9-tetramethyl-2-cyclo-undecyl-1-oxa-3,8-diaza-4-oxospiro [4,5]decane und epichlorohydrin.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and para-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl)methylphosphite, bis(2,4-di-tert-butyl-6-methylphenyl) ethylphosphite.

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridecyl-nitrone, N-hexadecyl-alpha-pentadecyl-nitrone, N-octadecyl-alpha-heptadecyl-nitrone, N-hexadecyl-alpha-heptadecyl-nitrone, N-octadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

11. Nucleatino, agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers ("ionomers").

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863, U.S. Pat. No. 4,338,244, U.S. Pat. No. 5,175,312, U.S. Pat. No. 5,216,052, U.S. Pat. No. 5,252,643, DE-A-4 316 611, DE-A-4 316 622, DE-A-4 316 876, EP-A-0 589 839 or EP-A-0 591 102 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]-phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one.

The costabilizers, with the exception of the benzofuranones mentioned under point 14, are added, for example, in concentrations of from 0.01 to 10%, based on the total weight of the material to be stabilized.

Other preferred compositions comprise, in addition to component (a) and the oligomeric compounds of the formula I, other additives, in particular phenolic antioxidants, light stabilizers and/or processing stabilizers.

Particularly preferred additives are phenolic antioxidants (point 1 in the list), sterically hindered amines (point 2.6 in the list), phosphites and phosphonites (point 4 in the list) and peroxide scavengers (point 8 in the list).

Other additives (stabilizers) which are likewise particularly preferred are benzofuran-2-ones, as described, for example, in U.S. Pat. No. 4,325,863, U.S. Pat. No. 4,338,244, U.S. Pat. No. 5,175,312, U.S. Pat. No. 5,216,052, U.S. Pat. No. 5,252,643, DE-A-4 316 611, DE-A-4 316 622, DE-A-4 316 876, EP-A-0 589 839 and EP-A-0 591 102.

Examples of such benzofuran-2-ones are compounds of the formula

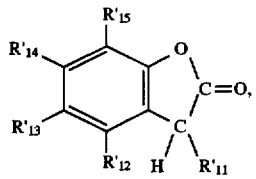

in which

R'$_{11}$ is an unsubstituted or substituted carbocyclic or heterocyclic aromatic ring system;

R'$_{12}$ is hydrogen;

R'$_{14}$ is hydrogen, alkyl having 1 to 12 carbon atoms, cyclopentyl, cyclohexyl or chlorine;

R'$_{13}$ is as defined for R'$_{12}$ or R'$_{14}$ or is a radical of the formula

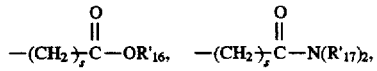

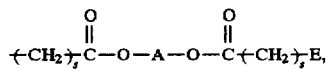

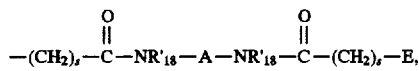

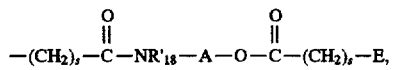

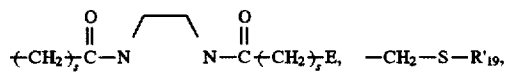

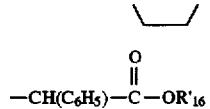

or -D-E, in which

R'$_{16}$ is hydrogen, alkyl having 1 to 18 carbon atoms, alkyl having 2 to 18 carbon atoms which is interrupted by oxygen or sulfur, dialkylaminoalkyl having a total of 3 to 16 carbon atoms, cyclopentyl, cyclohexyl, phenyl or phenyl which is substituted by 1 to 3 alkyl radicals having a total of at most 18 carbon atoms;

s is 0, 1 or 2;

the substituents R'$_{17}$, independently of one another, are hydrogen, alkyl having 1 to 18 carbon atoms, cyclopentyl, cyclohexyl, phenyl, phenyl which is substituted by 1 or 2 alkyl radicals having a total of at most 16 carbon atoms, a radical of the formula -C$_2$H$_4$OH,

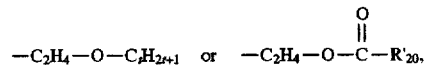

or, together with the nitrogen atom to which they are bonded, form a piperidine or morpholine radical;

t is from 1 to 18;

R'$_{20}$ is hydrogen, alkyl having 1 to 22 carbon atoms or cycloalkyl having 5 to 12 carbon atoms;

A is alkylene having 2 to 22 carbon atoms which may be interrupted by nitrogen, oxygen or sulfur;

R'$_{18}$ is hydrogen, alkyl having 1 to 18 carbon atoms, cyclopentyl, cyclohexyl, phenyl, phenyl which is substituted by 1 or 2 alkyl radicals having a total of at most 16 carbon atoms, or benzyl;

R'$_{19}$ is alkyl having 1 to 18 carbon atoms;

D is —O—, —S—, —SO—, —SO$_2$— or —C(R'$_{21}$)$_2$—; the substituents R'$_{21}$, independently of one another, are hydrogen, C$_1$-C$_{16}$alkyl, where the two R'$_{21}$ radicals together contain 1 to 16 carbon atoms, R'$_{21}$ is furthermore phenyl or a radical of the formula

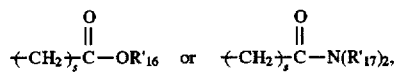

in which 1, R'$_{16}$ and R'$_{17}$ are as defined above;

E is a radical of the formula

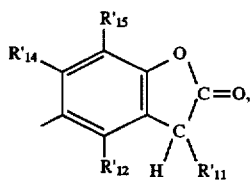

in which R'$_{11}$, R'$_{12}$ and R'$_{14}$ are as defined above; and R'$_{15}$ is hydrogen, alkyl having 1 to 20 carbon atoms, cyclopentyl, cyclohexyl, chlorine or a radical of the formula

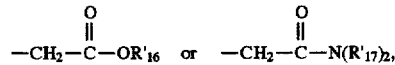

in which R'$_{16}$ and R'$_{17}$ are as defined above, or R'$_{15}$ together with R'$_{14}$ forms a tetramethylene radical.

Preference is given to benzofuran-2-ones in which R'$_{13}$ is hydrogen, alkyl having 1 to 12 carbon atoms, cyclopentyl, cyclohexyl, chlorine or a radical of the formula

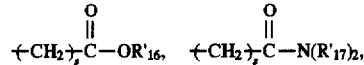

or —D—E, in which s, R'$_{16}$, R'$_{17}$, D and E are as defined above, and R'$_{16}$ is, in particular, hydrogen, alkyl having 1 to 18 carbon atoms, cyclopentyl or cyclohexyl.

Preference is also given to benzofuran-2-ones in which R'$_{11}$ is phenyl or phenyl which is substituted by 1 or 2 alkyl radicals having a total of at most 12 carbon atoms; R'$_{12}$ is hydrogen; R'$_{14}$ is hydrogen or alkyl having 1 to 12 carbon atoms; R'$_{13}$ is hydrogen, alkyl having 1 to 12 carbon atoms,

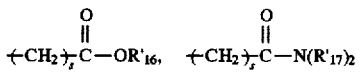

or —D—E;

R'$_{15}$ is hydrogen, alkyl having 1 to 20 carbon atoms,

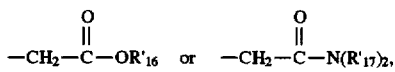

or R'$_{15}$ together with R'$_{14}$ forms a tetramethylene radical, where s, R'$_{16}$, R'$_{17}$, D and E are as defined at the outset.

Likewise of particular interest are benzofuran-2-ones in which R'$_{13}$ is hydrogen, alkyl having 1 to 12 carbon atoms or —D—E; R'$_{12}$ and R'$_{14}$, independently of one another, are hydrogen or alkyl having 1 to 4 carbon atoms; and R'$_{15}$ is alkyl having 1 to 20 carbon atoms, where D and E are as defined at the outset.

Finally, likewise of particular interest are benzofuran-2-ones in which R'$_{13}$ is alkyl having 1 to 4 carbon atoms or —D—E; R'$_{12}$ and R'$_{14}$ are hydrogen; and R'$_{15}$ is alkyl having 1 to 4 carbon atoms, cyclopentyl or cyclohexyl, where D is a -C(R'$_{21}$)$_2$-group and E is a radical of the formula

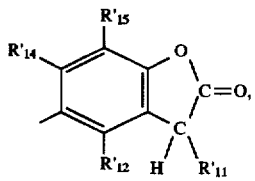

where the substituents R'$_{21}$ are identical or different and are each alkyl having 1 to 4 carbon atoms, and R'$_{11}$, R'$_{12}$, R'$_{14}$ and R'$_{15}$ are as defined above.

The amount of benzofuran-2-ones additionally employed can vary within broad limits. For example, they can be present in the novel compositions in amounts of from 0.0001 to 5% by weight, preferably from 0.001 to 2% by weight, in particular from 0.01 to 2% by weight.

The oligomeric compounds of the formula I and any further additives are incorporated into the polymeric, organic material by known methods, for example before or during shaping or alternatively by application of the dissolved or dispersed compounds to the polymeric, organic material, if necessary with subsequent evaporation of the solvent. The oligomeric compounds of the formula I can also be added to the materials to be stabilized in the form of a masterbatch, which contains these in, for example, a concentration from 2.5 to 25% by weight.

The oligomeric compounds of the formula I can also be added before or during polymerization or before crosslinking.

The oligomeric compounds of the formula I can be incorporated into the material to be stabilized in pure form o r encapsulated in waxes, oils or polymers.

The oligomeric compounds of the formula I can also be sprayed onto the polymer to be stabilized. They are capable of diluting other additives (for example the conventional additives mentioned above) or their melts, so that they can also be sprayed onto the polymer to be stabilized together with these additives. A particularly advantageous method is the addition by spraying during deactivation of the polymerization catalysts, where, for example, the s team us ed for deactivation can be used for the spraying.

In the case of polyolefins polymerized in bead form, it may, for example, be advantageous to apply the oligomeric compounds of the formula I, if desired together with other additives, by spraying.

The materials stabilized in this way can be used in a very wide variety of forms, for example as films, fibres, tapes, moulding compositions, profiles or as binders for paints, adhesives or adhesive cements.

As mentioned above, the organic materials to be protected are preferably organic polymers, particularly synthetic polymers. Thermoplastic materials, in particular polyolefins, are particularly advantageously protected. In particular, the excellent effectiveness of the oligomeric compounds of the formula I as processing stabilizers (heat stabilizers) should be emphasized. For this purpose, they are advantageously added to the polymer before or during processing thereof. However, other polymers (for example elastomers) or lubricants or hydraulic fluids can also be stabilized against degradation, for example lightinduced or thermo-oxidative degradation. Elastomers are given in the above list of possible organic materials.

Suitable lubricants and hydraulic fluids are based, for example, on mineral or synthetic oils or mixtures thereof. The lubricants are known to the person skilled in the art and are described in the relevant specialist literature, for example in Dieter Klamann, "Schmierstoffe und verwandte Produkte" [Lubricants and Related Products] (Verlag Chemie, Weinheim, 1982), in Schewe-Kobek, "Das Schmiermittel-Taschenbuch" [The Lubricant Handbook] (Dr. Alfred Hüithig-Verlag, Heidelberg, 1974) and in "Ullmanns Enzyklopädie der technischen Chemie"[Ullmann's Encyclopedia of Industrial Chemistry], Vol. 13, pages 85–94 (Verlag Chemie, Weinheim, 1977).

A preferred embodiment of the present invention is therefore the use of oligomeric compounds of the formula I and products obtainable by reacting a compound of the formula XXII or a mixture of compounds of the formula XXII with a compound of the formula XXIII or a mixture of compounds of the formula XXIII, for the stabilization of organic materials against oxidative, thermal or light-induced degradation.

The novel oligomeric compounds of the formula I are distinguished by pronounced excellent hydrolysis stability and advantageous colouring behaviour, ie low discoloration of the organic materials during processing.

Organic materials which have been stabilized by means of the compounds of the present invention are particularly well protected against light-induced degradation.

The present invention therefore also relates to a process for the stabilization of an organic material against oxidative, thermal or light-induced degradation, which comprises incorporating or applying at least one oligomeric compound of the formula I or at least a product obtainable by reacting a compound of the formula XXII or a mixture of compounds of the formula XXII with a compound of the formula XXIII or a mixture of compounds of the formula XXIII, into or to this material.

The examples below illustrate the invention in greater detail. Parts and percentages are by weight.

EXAMPLE 1

Preparation of the Oligomeric Compound (101)
(Table 1)

a) 3.57 g (26.0 mmol; 1.3 equivalents) of phosphorus trichloride are added dropwise, under nitrogen, at 50° C. to a stirred solution of 4.41 g (20.0 mmol) of 2,4-di-tert-butyl- 6-methylphenol and 50 mg (0.40 mmol) of 4-dimethylaminopyridine in 12 ml of toluene. After c. 5 minutes the reaction mixture is heated to 100° C. and stirred for 30 minutes at this temperature (end of HCl gas evolution). The solution is diluted with 12 ml of toluene. Excess phosphorus trichloride and c. 12 ml of toluene are then distilled off. The residue contains 2,4-di-tert-butyl-6-methylphenylphosphorodichloridite.

b) 42.47g (0.20 mol) of 4-n-butylamino-2,2,6,6-tetramethylpiperidine [EP-A-302 020, Example 1, page 4], 3 ml of concentrated hydrochloric acid and 300 ml of methanol are placed in a steel autoclave. The autoclave is blanketed with nitrogen. Then 26.5 g (0.60 mol) of ethylene oxide are introduced under pressure and the whole reaction mixture is heated to 150° C. The pressure is 10 bar. After 30 hours the reaction mixture is cooled to room temperature. Then c. 250 ml of methanol are distilled off and the residue is poured into an aqueous saturated solution of sodium hydrogencarbonate. After 3 extractions with ethyl acetate, the organic phases are washed with an aqueous saturated solution of sodium chloride, dried over sodium sulfate, and concentrated on a vacuum rotary evaporator. Chromatography of the residue on silica gel with the solvent system hexane/ethyl acetate 3:1 to 1:1 and ethyl acetate yields 31.5 g (53%) of 2-(n-butyl-[1-(2-hydroxyethyl)-2,2,6,6-tetramethylpiperidin-4-yl]amino)ethanol (compound (201)) as a pale yellow oil. Analysis: calcd: C 67.95%; H 12.08%; N 9.32%; found: C 67.31%; H 11.98%; N 9.10%.

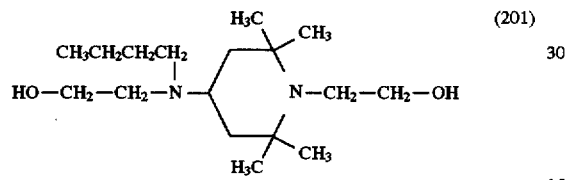

α) In accordance with the general procedure of Example 1b), the HALS diol (202) is prepared starting from the known 4-amino-1,2,2,6,6-pentamethylpiperidine [Beilstein EII, Vol. 22, page 321] with ethylene oxide; m.p. 57°–64° C. Analysis: calcd: C 65.07%; H 11.70%; N 10.84%; found: C 64.68%; H 11.43%; N 10.69%.

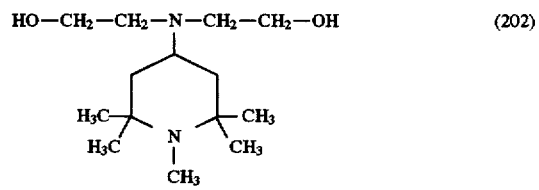

β) In accordance with the general procedure of Example 1b), the HALS diol (203) is prepared starting from the known bis(2,2,6,6-tetramethylpiperidin-4-yl)sebacate [®Tinuvin 770, Ciba-Geigy AG, U.S. Pat. No. 4,396,769] with ethylene oxide. Yield: 67%, m.p. 59–62° C., white powder. Analysis: calcd: C 67.57%, H 10.63%; N 4.92%; found: C 67.37%; H 10.67%; N 4.78%.

γ) 1.) 99.4 g (0.46 mol) of 4-n-butylamino-2,2,6,6-tetramethylpiperidine [EP-A-302 020, Example 1, page 4] are added dropwise at 15° C., under nitrogen, to a solution of 42.4 g (0.23 mol) of cyanuric chloride in 280 ml of xylene. The reaction mixture is stirred for 30 minutes at room temperature, then heated to c. 55° C., and a solution of 20 g (0.50 mol) of sodium hydroxide in 50 ml of water is added dropwise. When the dropwise addition is complete, the reaction mixture is stirred for a further 30 minutes at 55° C. The aqueous phase is separated, and the mixture is heated to 90° C. Simultaneously, 24 g (0.27 mol) of morpholine and a solution of 10 g (0.25 mol) of sodium hydroxide in 25 ml of water are added dropwise. The water is distilled off as an azeotrope. Then 50 ml of xylene are distilled off under a slight vacuum (115° C./0.7 torr). The reaction mixture is cooled to c. 50° C. and then washed twice with water. The organic phase is filtered over Hyflo. After addition of 50 ml of water and cooling to 5° C., 110 g (82%) of 2-N-morpholino-4,6-bis[N-n-butyl-(2,2,6,6-tetramethylpiperidin-4-yl)amino]-1,3,5-triazine crystallise out as a white powder of m.p. 112°–114° C. Analysis: calcd: C 67.53%; H 10.65%; N 19.09%; found: C 67.28%; H 10.70%; N 19.06%.

2.) In accordance with the general procedure of Example 1b), the HALS diol (204) is prepared starting from 2-N-morpholino-4,6-bis[N-n-butyl-(2,2,6,6-tetramethylpiperidin-4-yl)amino]-1,3,5-triazine (Example yl) with ethylene oxide; m.p. 114°–117° C. Analysis: calcd: C 65.84%; H 10.45%; N 16.60%. found: C 65.86%; H 10.33%; N 16.01%.

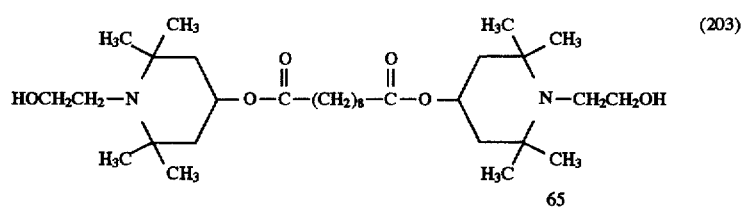

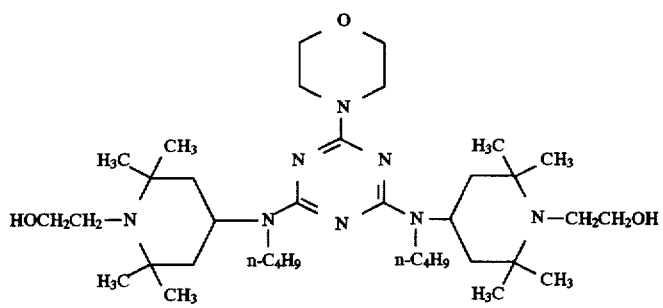

(204)

δ) 1.) 40.48 g (0.14 mol) of bis(2,2,6,6-tetramethylpiperidin-4-yl)amine [EP-A-336 895, Ciba-Geigy] and 11.4 g (0.14 mol) of a 36% aqueous solution of formaldehyde are placed in a 200 ml sulfonation flask. Then 25.8 g (0.56 mol) of formic acid are added dropwise at room temperature. In the course of this addition the temperature in the reactor rises to 70° C., with evolution of $CO_2$. The reaction mixture is then further stirred until it has cooled to room temperature. The aqueous phase is saturated with potassium carbonate and the reaction mixture is extracted 3 times with chloroform. The organic phases are combined, dried over potassium carbonate and concentrated on a vacuum rotary evaporator. Chromatography of the residue on silica gel with the solvent system hexane/dichloromethane 9:1+5% triethylamine yields 21 g (49%) of methyl-bis(2,2,6,6-tetramethylpiperidin-4-yl)amine, m.p. 51°–53° C., as a white powder. $^1$H-NMR (300 MHz, $CDCl_3$):δ=2.25 ppm (s, 3H) methyl group at the nitrogen.

2.) In accordance with the general procedure of Example 1b), the HALS diol (205) is prepared starting from methyl-bis(2,2,6,6-tetramethyl-piperidin-4-yl)amine (Example δ1) with ethylene oxide. Analysis: calcd:C 69.47%; H 11.91%; N 10.57%; found: C 68.31%; H 12.16%; N 10.50%.

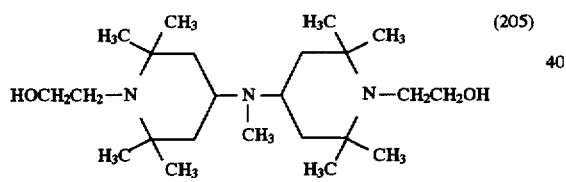

(205)

ε) The HALS diol (206) is known and the preparation is described in U.S. Pat. No. 4,210,576, page 5, Example 1.

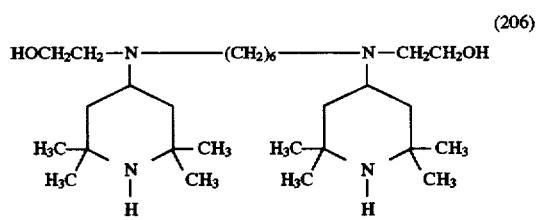

(206)

φ) 1.) 63.5 g (0.195 mol) of a 21% solution of sodium methylate in toluene are added dropwise at room temperature and under nitrogen to a solution of 69.7 g (0.13 mol) of 2,4-bis[N-(2,2,6,6-tetramethyl-4-piperidinyl)butylamino]-6-chloro-1,3,5-triazine [EP-A-314 472, Sankyo] in 400 ml of toluene. The reaction mixture is then refluxed for 20 hours. After cooling to room temperature, the reaction mixture is washed successively with water, 1N sodium hydrogencarbonate solution, water, and a saturated solution of sodium chloride. The organic phases are combined, dried over potassium carbonate, and concentrated on a vacuum rotary evaporator. Crystallisation of the residue from acetonitrile yields 52.2 g (74%) of 2-ethoxy-4,6-bis[N-(2,2,6,6-tetramethyl-4-piperidinyl)butylaminol-]1,3,5-triazine, m.p. 95°–104° C., white powder. $^1$H-NMR (300 MHz, $CDCl_3$): δ=4.345 ppm (q, J=7 Hz)—$OCHCH_3$.

2.) 38.5 g (0.07 mol) of 2-ethoxy-4,6-bis[N-(2,2,6,6-tetramethyl-4-piperidinyl)butylamino]-1,3,5-triazine (Example φ1), 140 ml of ethanol and 70 ml of water are placed in a 1 l autoclave. The autoclave is blanketed with nitrogen. Then 12.4 g (0.28 mol) of ethylene oxide are introduced under pressure and the reaction mixture is heated to 90° C. (pressure=2 bar). After 2 hours the reaction mixture is cooled to 30° C. and 12.4 g (0.2g mol) of ethylene oxide are again introduced under pressure. The reaction mixture is heated to 100° C. and kept at this temperature for 3 hours (pressure=3 bar). After cooling to room temperature, the reaction mixture is concentrated on a vacuum rotary evaporator. The residue is dissolved in 100 ml of acetonitrile and filtered hot. Upon cooling, 40 g (90%) of the HALS diol (207) crystallise out as a white powder of m.p. 160°–170° C. Analysis: calcd: C 66.31%; H 10.65%; N 15.47%; found: C 66.23%); H 10.61%; N 15.34%.

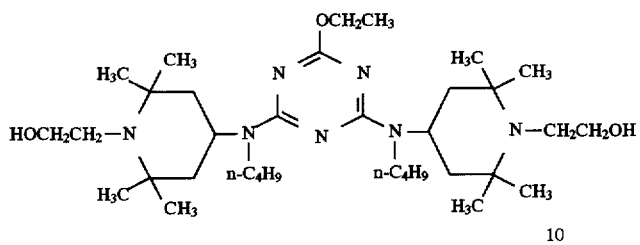

η) 1.) 16.5 g (0.21 mol) of acetyl chloride are added dropwise at 12°–13° C., under nitrogen, to a solution of 42.5 g (0.20 mol) of 4-n-butylamino-2,2,6,6-tetramethylpiperidine [EP-A-302 020, Example 1, page 4] and 50 ml (36.3 g; 0.36 mol) of triethylamine in 300 ml of toluene. The reaction mixture is stirred for 3 hours at room temperature. The precipitated triethylamine hydrochloride is removed by filtration and the filtrate is concentrated on a vacuum rotary evaporator. Distillation of the residue (90–92° C., 005 mbar) yields 38.7 g (76%) of N-n-butyl-N-(2,2,6,6-tetramethyl-4-piperidinyl)acetamide as a viscous oil.

2.) In accordance with the general procedure of Example 1bφ2, reaction of 25.4 g (0.10 mol) of N-n-butyl-N-(2,2,6,6-tetramethyl-4-piperidinyl)-acetamide [Example 1bη1] and 17.6 g (0.40 mol) of ethylene oxide in (100 ml of water and 100 ml of ethanol yields 27.2 g of crude product. Chromatography on silica gel with the solvent system ethyl acetate/ethanol/triethylamine=30: 1: yields. 17.2 (58%) of the desired N-n-butyl-N-[1-(2-hydroxyethyl)-2,2,6,6-tetramethylpiperidin-4-yl] acetamide as a viscous oil which solidifies on storage; m.p. 72°–82° C. Analysis: calcd: C 68.41%; H 11.48%; N 9.39%. Analysis: found: C 67.99%; H 11.96%; N 9.14%.

3.) A solution of 12.6 g (42.2 mmol) of N-n-butyl-N-[1-(2-hydroxyethyl)-2,2,6,6-tetramethylpiperidin-4-yl] acetamide [Example 1bη2] in 180 ml of 2N hydrochloric acid is refluxed for 48 hours. The reaction mixture is then cooled 0°–5 C. and, after addition of 40 ml of 30% sodium hydroxide solution, extracted twice with toluene. The organic phases are washed with water, combined, dried over sodium sulfate, and concentrated on a vacuum rotary evaporator. Chromatography of the residue on silica gel with the solvent system ethyl acetate/ethanol/triethylamine=50:2:1 yields 8.1 g (68%) of 2-(4-n-butylamino-2,2,6,6-tetramethylpiperidin-1-yl) ethanol (208) as a white powder of m.p. 106°–111° C. Analysis: calcd: C 70.26%; H 12.58%; N 10.92%. found: C 70.42%; H 12.85%; N 11.00%.

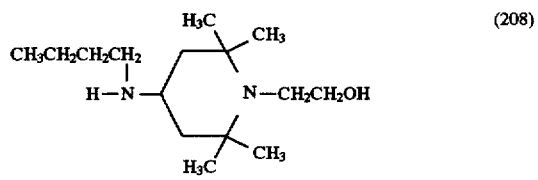
(208)

τ) 833 g (5.30 mol) of 4-hydroxy-2,2,6,6-tetramethylpiperidine and 418 g (1.05 mol) of 2-butyne-1,4-diol-ditosylate [C.A. Registry No. 6337-59-3] in 3.6 l of acetonitrile are placed, under argon, in a round-bottomed flask equipped with magnetic stirrer and condenser. The reaction mixture is refluxed overnight, then cooled, poured on ice and extracted repeatedly with ethyl acetate. The organic phases are combined, dried over sodium sulfate and concentrated on a vacuum rotary evaporator. Crystallisation of the residue from ethanol yields 295 g (76%) of 1,4-bis (4-hydroxy-2,2,6,6-tetramethylpiperidin-1-yl)-but-2-yne (209), m.p. 203.4° C., in the form of white crystals. Analysis: calcd: C 72.48%; H 11.06%; N 7.68%. found: C 72.52%; H 11.12%; N 7.75%.

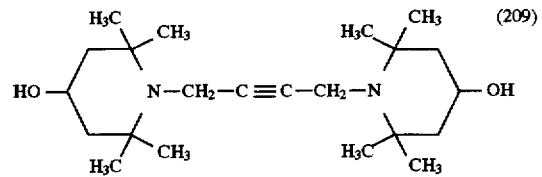
(209)

κ) The HALS diol (210) is known and described in U.S. Pat. No. 4,569,997 (Ciba-Geigy, Example 1, column 14).

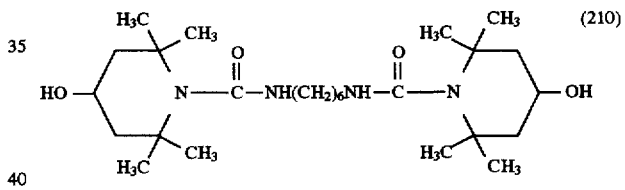
(210)

λ)1.) 9.15 g (50 mmol) of adipyl dichloride are added dropwise at 0°–5° C., under nitrogen, to a stirred solution of 22.2 g (105 mmol) of 4-n-butylamino-2,2,6,6-tetramethylpiperidine [EP-A-302 020, Example 1, page 41 in 70 ml of triethylamine and 150 ml of toluene. After c. 30 minutes the reaction mixture is heated to c. 100° C. and stirred for 90 minutes at this temperature. The resultant dense suspension is thereafter cooled to room temperature, filtered to remove the salts, and the filtrate is concentrated on a vacuum rotary evaporator. Chromatography of the residue on silica gel with the solvent system ethyl acetate/ethanol/triethylamine=20:1:1 and crystallisation of the pure fractions from hexane yields 17.15 g (64%) of N,N'-di-n-butyl-N,N'-bis-(2,2,6,6-tetramethyl-4-piperidinyl)hexane diamide as a white powder; m.p. 134°–144° C.

2.) In accordance with the general procedure of Example 1bφ2, the HALS diol (211) is prepared starting from N,N'-di-n-butyl-N,N'-bis(2,2,6,6-tetramethyl-4-piperidinyl)-hexanediamide [Example 1b λ1] with ethylene oxide. Analysis: calcd: C 69.41%; H 11.33%; N 8.99%. found: C 68.45%; H 11.20%; N 8.34%.

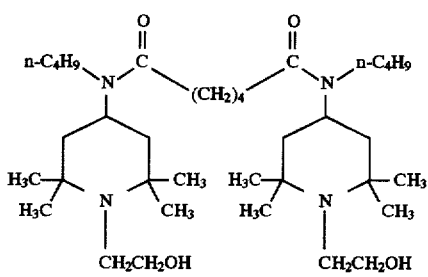
(211)

μ) 3.45 g (18 mmol) of adipyl dichloride are added dropwise at c. −10° C., under nitrogen, to a stirred solution of 8.4 g (39 mmol) of 4-(2-hydroxyethylamino)-1,2,2,6,6-pentamethylpiperidine [U.S. Pat. No. 3,904,581, Sankyo] in 25 ml of triethylamine and 50 ml of toluene. The reaction mixture is stirred for 1 hour at 70° C., then cooled to room temperature, filtered, and the filtrate is concentrated on a vacuum rotary evaporator. Chromatography of the residue over silica gel with the solvent system ethyl acetate/ethanol/triethylamine=20:1:1 yields 4.9 g (51%) of the desired HALS diol (212) as a resin.

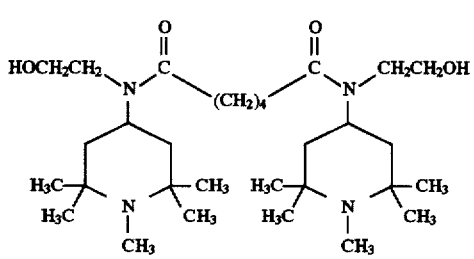
(212)

v) 1.) 9.9 g (126 mmol) of acetyl chloride are added dropwise at c. 5° C., under nitrogen, to a stirred solution of 26.6 g (57 mmol) of N,N'-bis(2,2,6,6-tetramethyl-4-piperidinyl)-1,6-hexane diamine [U.S. Pat. No. 5,187,275, Example 3] in 42 ml (0.30 mol) of triethylamine and 100 ml of toluene. The reaction mixture is stirred for 1 hour at room temperature and for 1 hour at c. 45° C. and then concentrated on a vacuum rotary evaporator. The residue is taken up in methylene chloride and the organic phase is washed with a 15% aqueous solution of sodium hydroxide and water. The organic phase is dried over potassium carbonate and concentrated on a vacuum rotary evaporator. Crystallisation of the residue from acetone yields 12.6 g (47%) of N,N'-hexanediylbis(2,2,6,6-tetramethyl-4-piperidinyl)acetamide in the form of a beige powder (m.p. 149°–154° C.).

2.) In accordance with the general procedure of Example 1bφ2, the HALS diol (213) is prepared starting from N,N'-hexanediylbis(2,2,6,6-tetramethyl-4-piperidinyl)acetamide [Example 1b v1] with ethylene oxide; m.p. 200°–205° C. Analysis: calcd: C 67.80%; H 11.02%; N 9.88%. found: C 67.70%; H 11.22%; N 9.89%.

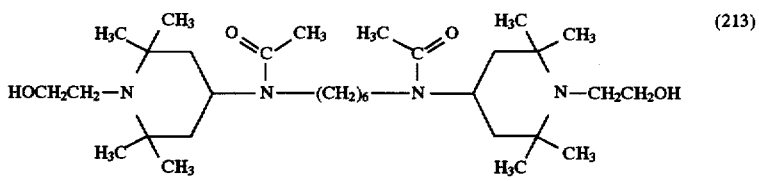
(213)

ω) 12.1 g (47.0 mmol) of 9-aza-3-hydroxymethyl-3,8,8,10,10-pentamethyl-1,5-dioxospiro[5.5]undecane (DE-A-2 353 538, Sankyo, Example 1, page 38), 50 ml of ethanol and 50 ml of water are placed in a 1l autoclave. The autoclave is blanketed with nitrogen, then 8.2 g (188 mmol) of ethylene oxide are introduced under pressure and the reaction mixture is heated to 90° C. (pressure=2 bar). After 2 hours, the reaction mixture is cooled to 30° C. and a further 8.2 g (188 mmol) of ethylene oxide are introduced under pressure. The reaction mixture is heated to 100° C. and kept for 3 hours at this temperature (pressure=3 bar). After cooling to room temperature, the reaction mixture is concentrated on a vacuum rotary evaporator. The residue is dissolved in ethyl acetate and chromatographed on silica gel with ethyl acetate as eluant. Crystallisation of the pure fractions from toluene/hexane=9:1 yields 11.15 g (79%) of HALS diol (214); m.p. 110°–115° C., as a white powder. Analysis: calcd: C 63.76%; H 10.37%; N 4.65%. found: C 64.04%; H 10.32%; N 4.45%.

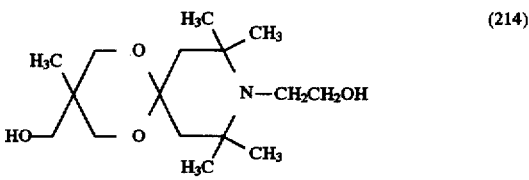
(214)

π) The HALS diol (215) is likewise known and the preparation is described in JP-A-57 21 368 (Adeka Argus, Example 7).

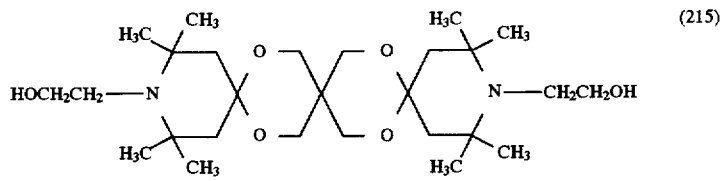

(215)

c) 7.81 g (26.0 mmol; 1.3 equivalents) of HALS diol (201) (Example 1b), 5.06 g (50.0 mmol, 2.5 equivalents) of triethylamine and 130 ml of toluene are placed, under nitrogen, in a 350 ml sulfonation flask. The above described solution (Example 1a) is added dropwise to this colourless solution at 50° C. over 20 minutes. The dense suspension is heated to 100° C. and further stirred for 3 hours at this temperature. The reaction mixture is cooled to room temperature and filtered over Celite. The filtrate is concentrated on a vacuum rotary evaporator. The residue is dried under a high vacuum, yielding 12.8 g (100%) of the oligomeric compound (101) (Table 1) as a viscous oil.

In accordance with the general procedure of Example 1c, the oligomeric compound (102) (Table 1) is prepared from the HALS diol (202).

EXAMPLE 2

Preparation of the Oligomeric Compound (103)
(Table 1).

a) In accordance with the general procedure of Example 1a, the corresponding dichlorophosphite solution is prepared from 3.3 g (15.0 mmol) of 2,4-di-tert-butyl-6-methylphenol, 1.7 ml (20.0 mmol; 1.3 equivalents) of phosphorus trichloride and 37 mg (0.30 mmol) of 4-dimethylaminopyridine in 10 ml of toluene. b) 5.86 g (19.5 mmol; 1.3 equivalents) of the HALS diol (201) (Example 1b), 24 ml of triethylamine and 24 ml of toluene are placed in a 100 ml sulfonation flask under nitrogen. The above described solution (Example 2a) is then added dropwise to this solution at 45° C. over 15 minutes. The dense suspension is heated to 100° C. and further stirred for 3 hours at this temperature. The reaction mixture is cooled to room temperature and filtered over Celite. The filtrate is concentrated on a vacuum rotaray evaporator and the residue is dried under a high vacuum, yielding 9.60 g (100%) of the oligomeric compound (103) (Table 1) as a viscous oil.

In accordance with the general procedure of Example 2, the oligomeric compounds (104), (105), (106), (107) and (108) are prepared from the corresponding HALS diols (203), (204), (205), (206) and (207) (Table 1).

EXAMPLE 3

Preparation of the Oligomeric Compound (109)
(Table 1).

5.17 g (9.10 mmol; 1.3 equivalents) of the HALS diol (203) (Example 1bβ), 15 ml of triethylamine and 15 ml of toluene are placed in a 100 ml sulfonation flask under nitrogen. Then 1.26 g (7.0 mmol) of phenyl dichlorophosphine are added dropwise to this solution at room temperature. The white suspension is heated to 100° C. and further stirred for 3 hours at this temperature. The reaction mixture is cooled to room temperature and filtered over Celite. The filtrate is concentrated on a vacuum rotaray evaporator and the residue is dried under a high vacuum, yielding 6.0 g (100%) of the oligomeric compound (109) (Table 1) as a viscous oil.

The oligomeric compounds (110), (111), (112), (113), (114) and (115) are prepared as described in Example 3 from the corresponding HALS diols (204), (209), (205), (210), (211) and (207) (Table 1).

EXAMPLE 4

Preparation of the Oligomeric Compound (116)
(Table 1).

a) In accordance with the general procedure of Example 1a, the corresponding dichlorophosphite solution is prepared from 1.77 g (8.03 mmol) of 2,4-di-tert-butyl-6-methylphenol, 1.43 g (10.4 mmol; 1.3 equivalents) of phosphorotrichloride and 16 mg (0.13 mniol) of 4-dimethylaminopyridine in 5 ml of toluene.

b) 5.5 g (8.83 mmol; 1.1 equivalents) of the HALS diol (211) [Example 1bλ2], 18 ml of triethylamine and 13 ml of toluene are placed in a 100 ml sulfonation flask under nitrogen. The above described solution (Example 4a) is then added dropwise to this solution at 45° C. over 13 minutes. The dense suspension is afterwards refluxed for 3 hours. The reaction mixture is diluted with 10 ml of toluene, cooled to room temperature, and filtered over Hyflo. The filtrate is concentrated on a vacuum rotaray evaporator and the residue is dried under a high vacuum, yielding 7.3 g (97%) of compound (116) (Table 1), m.p. 82°–91° C., as an amorphous white powder.

In accordance with the general procedure of Example 4, the oligomeric compounds (117), (118), (119), (121) and (123) (Table 1) are prepared from the corresponding HALS diols (212), (213), (214) and (215) and the amino alcohol (208).

EXAMPLE 5

Preparation of the Oligomeric Compound (120)
(Table 1).

4.42 g (7.8 mmol; 1.1 equivalents) of the HALS diol (213) [Example 1bv2 ], 10 ml of triethylamine and 8 ml of toluene are placed in a 100 ml sulfonation flask under nitrogen. A solution of 1.27 g (7.09 mmol) of phenyl dichlorophosphine in 2 ml of toluene is added dropwise to this solution at 45° C. over 5 minutes. The suspension is then refluxed for 3 hours. The reaction mixture is diluted with 4 ml of toluene, cooled to room temperature, and filtered over Celite. The filtrate is concentrated on a vacuum rotaray evaporator and the residue is dried under a high vacuum, yielding 5 g (97%) of the oligomeric compound (120) as an amorphous pale beige powder, m.p. 92°–105° C. (Table 1).

The oligomeric compound (122) is prepared from the FIALS diol (215) as described in Example 5.

TABLE 1
| Nr. | Compound | L | Mn | Mw/Mn | m.p. (°C.) | % P (cal./found) |
|---|---|---|---|---|---|---|
| 101 | 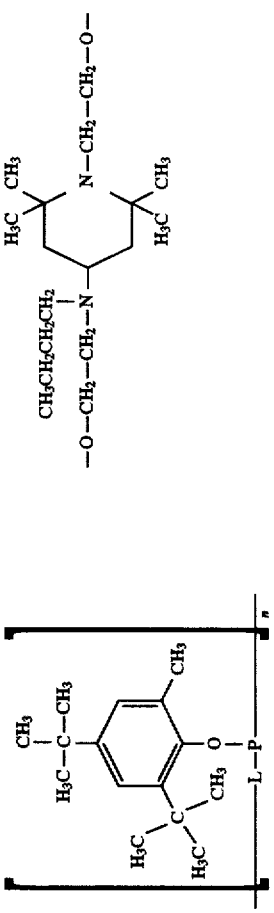 | —O—CH$_2$—CH$_2$—N(CH$_2$CH$_2$CH$_3$)—[2,2,6,6-tetramethyl-4-piperidyl with N—CH$_2$—CH$_2$—O—]— | 1246[a] | 2.10[a] | — | 4.85 / 4.33 |
| 102 | 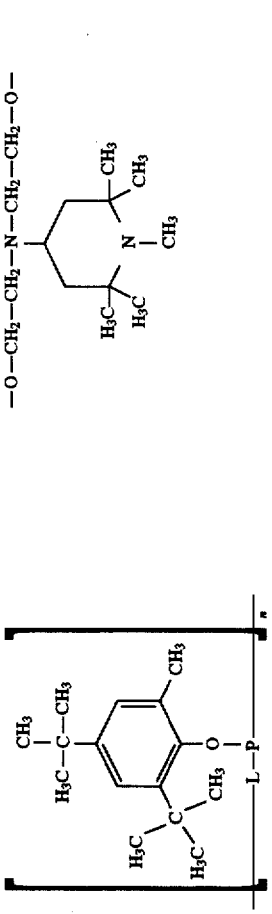 | —O—CH$_2$—CH$_2$—N(CH$_3$)—[2,2,6,6-tetramethyl-4-piperidyl]—CH$_2$—CH$_2$—O— | 607[a] | 1.60[a] | — | 5.30 / 4.90 |
| 103 | 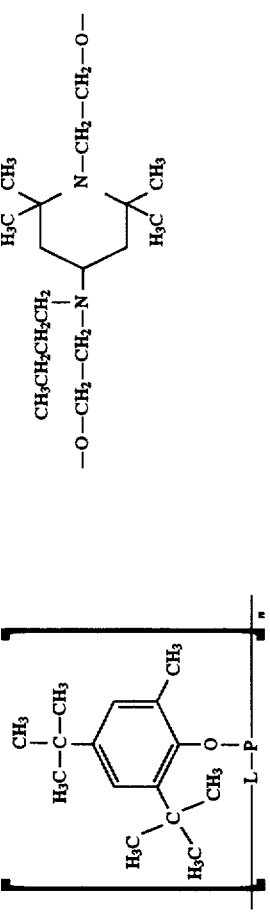 | —O—CH$_2$—CH$_2$—N(CH$_2$CH$_2$CH$_3$)—[2,2,6,6-tetramethyl-4-piperidyl with N—CH$_2$—CH$_2$—O—]— | 1059[a] | 3.70[a] | — | 4.85 / 4.08 |

TABLE 1-continued

| Nr. | Compound | L | Mn | Mw/Mn | m.p. (°C.) | % P (cal/found) |
|---|---|---|---|---|---|---|
| 104 | [structure with phenol-O-L-P]$_n$ | bis-piperidine structure with R$_{12}$ = —O—C(=O)—(CH$_2$)$_8$—C(=O)—O— | 2614[a] | 5.20[a] | 55–58 | 3.14 / 3.03 |
| 105 | [structure with phenol-O-L-P]$_n$ | bis-piperidine structure | 1988[a] | 3.80[a] | 130–137 | 2.75 / 2.38 |
| 106 | [structure with phenol-O-L-P]$_n$ | morpholine-triazine structure with R$_{12}$ = CH$_3$CH$_2$CH$_2$ | 550[a] | 1.74[a] | — | 4.05 / 3.91 |

TABLE 1-continued
| Nr. | Compound | L | Mn | Mw/Mn | m.p. (°C.) | % P (cal./found) |
|---|---|---|---|---|---|---|
| 107 |  | —O—CH₂—CH₂—N(R₁₃)—CH₂—CH(CH₂C(CH₃)₂NH)(CH₂C(CH₃)₂)—N—CH₂—CH₂—O— ; R₁₃ = —(CH₂)₆— | 1158[b] | 1.15[b] | — | 3.54 / 3.52 |
| 108 | 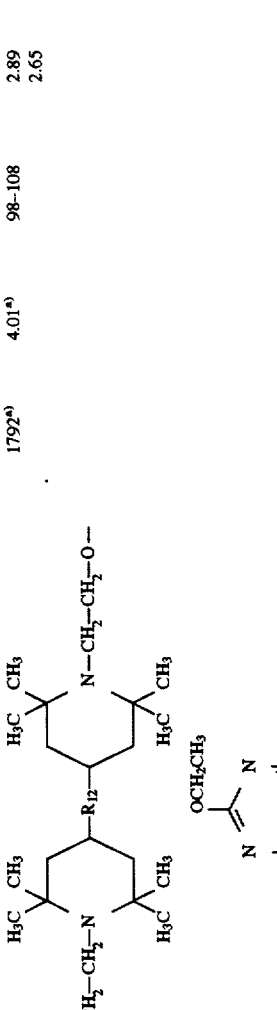 | Bis-piperidinyl triazine linker with R₁₂ = CH₃CH₂CH₂CH₂ | 1792[a] | 4.01[a] | 98–108 | 2.89 / 2.65 |
| 109 | 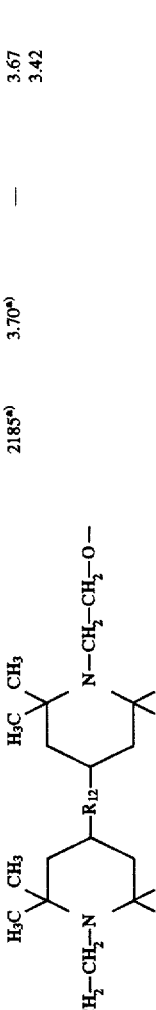 | Bis-piperidinyl linker with R₁₂ = —O—C(O)—(CH₂)₈—C(O)—O— | 2185[a] | 3.70[a] | — | 3.67 / 3.42 |

TABLE 1-continued
| Nr. | Compound | L | Mn | Mw/Mn | m.p. (°C.) | % P (cal/ found) |
|---|---|---|---|---|---|---|
| 110 | 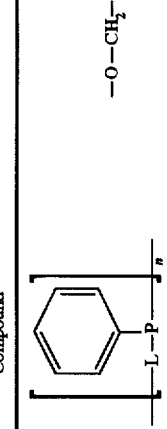 |  | 1787[a] | 3.80[a] | 130–142 | 3.15 3.09 |
| 111 | 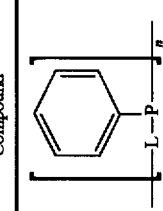 | 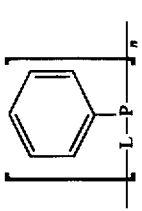 | 1568[a] | 4.40[a] | 102–110 | 5.35 5.86 |
| 112 | 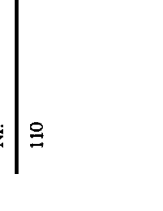 |  | 479 | 1.62 | Harz | 4.98 4.82 |

TABLE 1-continued

| Nr. | Compound | L | Mn | Mw/Mn | m.p. (°C.) | % P (cal./found) |
|---|---|---|---|---|---|---|
| 113 | [phenyl-L-P]$_n$ | Structure with two 2,2,6,6-tetramethylpiperidine rings linked via N—R$_{17}$—N, with —O— substituents; R$_{17}$ = —C(=O)—NH—(CH$_2$)$_6$—NH—C(=O)— | 368 | 2.12 | 75–85 | |
| 114 | [phenyl-L-P]$_n$ | Structure with two 2,2,6,6-tetramethylpiperidine rings (N—CH$_2$—CH$_2$—O—, N—CH$_3$) connected via R$_{12}$, with —O—CH$_2$—CH$_2$— linkages; R$_{12}$ = n-C$_4$H$_9$—N—C(=O)—(CH$_2$)$_4$—C(=O)—N—n-C$_4$H$_9$ | 1921 | 2.64 | 65–77 | |
| 115 | [phenyl-L-P]$_n$ | Structure with two 2,2,6,6-tetramethylpiperidine rings (N—CH$_2$—CH$_2$—O—, N—CH$_3$) connected via R$_{12}$, with —O—CH$_2$—CH$_2$— linkages; R$_{12}$ = triazine with OCH$_2$CH$_3$ and two N(CH$_2$CH$_2$CH$_3$) groups | 1731 | 2.06 | 108–122 | |

TABLE 1-continued

| Nr. | Compound | L | Mn | Mw/Mn | m.p. (°C.) | % P (cal/found) |
|---|---|---|---|---|---|---|
| 116 | | structure with R₁₂ linker, piperidine groups, N—CH₂—CH₂—O—; R₁₂ = —n-C₄H₉, amide with —(CH₂)₄— | 2347 | 4.66 | 82-91 | 3.31 / 3.17 |
| 117 | | structure with R₁₃ linker; R₁₃ = —C—(CH₂)₄—C— (diketo) | 660 | 2.07 | 50-58 | |
| 118 | | structure with R₁₂ linker, piperidine groups; R₁₂ = —N—(CH₂)₆—N— (urea) | 2234 | 9.2 | 98-113 | |

TABLE 1-continued
| Nr. | Compound | L | Mn | Mw/Mn | m.p. (°C.) | % P (cal./ found) |
|---|---|---|---|---|---|---|
| 119 | 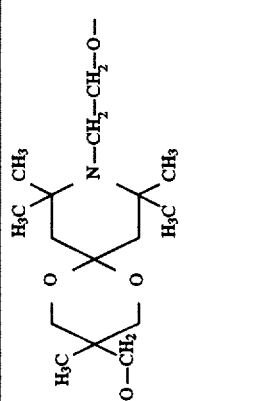 | 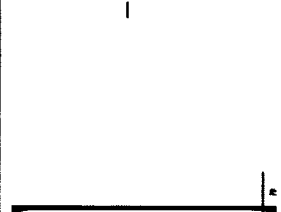 | 2327 | 4.3 | 93–101 | |
| 120 | 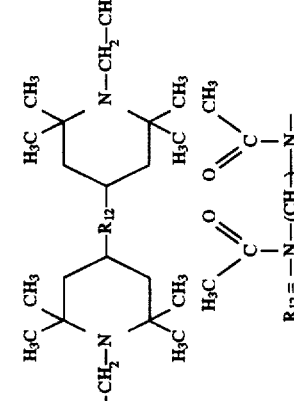 | 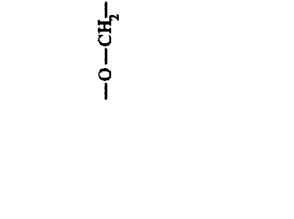 | 2149 | 2.88 | 92–105 | 4.25 4.26 |
| 121 | 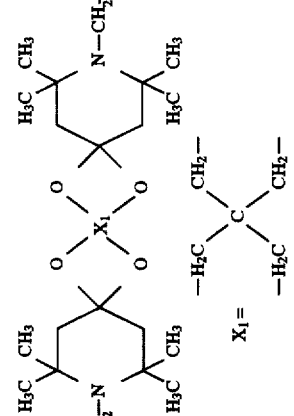 | 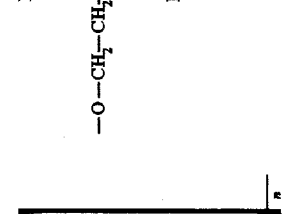 | 1620 | 8.6 | 105–125 | |

TABLE 1-continued

| Nr. | Compound | L | Mn | Mw/Mn | m.p. (°C.) | % P (cal/found) |
|---|---|---|---|---|---|---|
| 122 | ![structure](phenyl-L-P repeat unit) | —O—CH₂—CH₂—N(H₃C)(CH₃)(ring)(H₃C)(CH₃)—N—CH₂—CH₂—O— with X₁ bridge; X₁ = —H₂C—C(CH₂—)(CH₂—)—CH₂—; and CH₃CH₂CH₂CH₂—N(piperidine with H₃C CH₃ / H₃C CH₃)—N—CH₂—CH₂—O— | 1909 | 2.34 | 100-125 | |
| 123 | ![structure with tert-butyl substituted phenol L-P repeat] | | 690 | 1.62 | 52-59 | |

Mn = number average molecular weight.
Mw = weight average molecular weight.
a) determination by GPC (gel permeation chromatography).
b) determination by MALDI ("Matrix Assisted Laser Desorption Ionisation").

EXAMPLE 6

Stabilisation of Multiple-Extruded Polypropylene 1.3 kg of polypropylene powder (Profax®86501) which has been prestabilised with 0.025% of Irganox ® 1076 (n-octadecyl (3-[3,5-di-tert-butyl-4-hydroxyphenyl] propionate] (having a melt index of 3.2 measured at 230°/ 216 kg), are blended with 0.05% of Irganox® 1010 (pentaerythrityl tetrakis-[3-(3,5-di-tert-butyl-4-hydroxyphenyl)propionate), 0.05% of calcium stearate, 0.03% of dihydrotalcite [DHT 4A®,Kyowa Chemical Industry Co., Ltd., $Mg_{4.5}Al_2(OH)_{13}CO_3.3.5\ H_2O$ ] and 0.05% of compound of Table 1. This blend is then extruded at 100 rpm in an extruder having a cylinder diameter of 20 mm and a length of 400 mm, the 3 heating zones being adjusted to the following temperatures: 260° C., 270° C., 280° C. The extrudate is cooled by drawing it through a water bath and then granulated. This granulate is repeatedly extruded. The melt index is measured after 3 extrusions (230° C./2.16 kg). A substantial increase in the melt index denotes pronounced chain degradation, i.e. poor stabilisation. The results are shown in Table 2.

TABLE 2

| Compound of Table 1 | Melt index after 3 extrusions |
|---|---|
| — | 18.2 |
| 102 | 7.4 |
| 103 | 6.8 |
| 104 | 8.5 |
| 105 | 8.7 |
| 106 | 6.9 |
| 109 | 7.2 |
| 110 | 7.0 |
| 113 | 5.9 |
| 114 | 8.9 |
| 118 | 8.3 |
| 119 | 6.8 |
| 120 | 6.5 |
| 122 | 7.5 |

What is claimed is:

1. An oligomeric compound of formula I $$\left[\begin{array}{c} R_1 \\ | \\ (O)_m \\ | \\ L-P \end{array}\right]_n \quad (I)$$

wherein L is a group of formula II or III (III) [structure with $H_3C$, $CH_3$, $R_4$, $N$, $N-R_3-O-$]

$R_1$ is $C_1-C_{25}$alkyl, $C_2-C_{25}$alkyl which is interrupted by oxygen, sulfur or >N—$R_5$; $C_2-C_{24}$-alkenyl, unsubstituted or $C_1-C_4$alkyl-substituted $C_5-C_{15}$cycloalkyl; unsubstituted or $C_1-C_4$-alkyl-substituted $C_5-C_{15}$cycloalkenyl; $C_7-C_9$phenylalkyl which is unsubstituted or substituted at the phenyl ring by $C_1-C_4$alkyl; or tetrahydroabietyl; or $R_1$ is a radical of formula IV (IV) [structure with $R_6$, $R_9$, $R_7$, $R_8$ on phenyl ring]

$R_2$ is a group of formula V to VIII and XII (V) [piperidine structure with $R_3-N-R_3$, $H_3C$, $CH_3$, $R_{10}$]

(VI) [bis-piperidine structure with $R_{11}$, $R_3-N$, $N-R_3$]

(VII) [bis-piperidine structure with $R_3-N$, $R_{12}$, $N-R_3$]

(VIII) [bis-piperidine structure with $R_3-N$, $R_{13}$, $N-R_3$, $R_{10}$]

(XII) [bis-piperidine structure with $N-R_{17}-N$]

$R_3$ is $C_1-C_{18}$alkylene, $C_2-C_{18}$alkylene which is interrupted by oxygen, sulfur or >N—$R_5$;
$C_4-C_8$alkenylene or phenylethylene,
$R_4$ is $C_1-C_8$alkyl or a radical of formula XVII (XVII) [piperidine structure with $CH_3$, $N-R_{10}$]

$R_5$ is hydrogen or $C_1-C_8$alkyl,
$R_6$ and $R_7$ are each independently of the other hydrogen, $C_1-C_{25}$alkyl, $C_2-C_{24}$alkenyl, unsubstituted or $C_1-C_4$alkyl-substituted $C_5-C_8$cycloalkyl; unsubstituted or $C_1-C_4$alkyl-substituted phenyl; unsubstituted or $C_1-C_4$alkyl-substituted $C_5-C_8$cycloalkenyl; $C_7-C_9$phenylalkyl or —$CH_2$—S—$R_{20}$,
$R_8$ is hydrogen or methyl, $R_9$ is hydrogen, $C_1$-$C_{25}$alkyl, $C_2$-$C_{24}$alkenyl, unsubstituted or $C_1$-$C_4$alkyl-substituted $C_5$-$C_8$cycloalkyl; unsubstituted or $C_1$-$C_4$alkyl-substituted phenyl; unsubstituted or $C_1$-$C_4$—alkyl-substituted $C_5$-$C_8$cycloalkenyl; $C_7$-$C_9$phenylalkyl, —$CH_2$—S—$R_{20}$, —$(CH_2)_pCOOR_{21}$ or —$(CH_2)_qOR_{22}$.

$R_{10}$ is hydrogen, $C_1$-$C_8$alkyl, oxygen free radical, OH, NO, —$CH_2CN$, $C_1$-$C_{18}$alkoxy, $C_5$-$C_{12}$cycloalkoxy, $C_3$-$C_6$alkenyl, $C_3$-$C_6$alkynyl, $C_1$-$C_8$acyl, $C_7$-$C_9$phenylalkyl which is unsubstituted or substituted at the phenyl ring by $C_1$-$C_4$alkyl.

$R_{11}$ is $C_1$-$C_8$alkyl or a radical of formula XVII

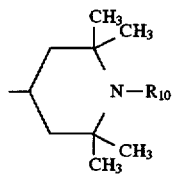
(XVII)

$R_{12}$ is 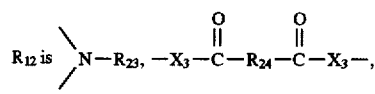

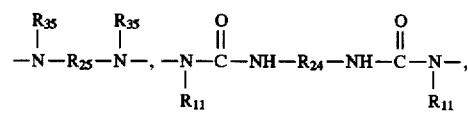

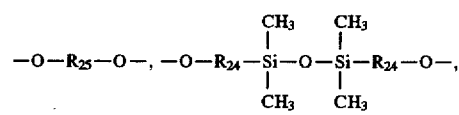

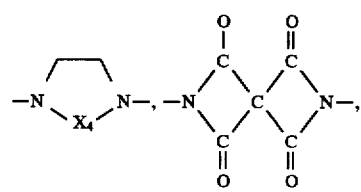

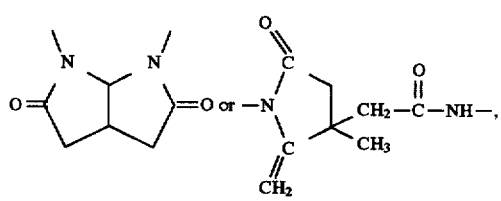

$R_{13}$ is 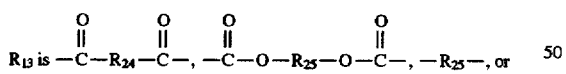

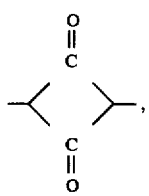

$R_{17}$ is

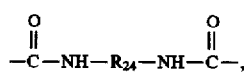

$C_1$-$C_{18}$-alkylene, $C_2$-$C_{18}$alkylene which is interrupted by oxygen, sulfur or >N—$R_5$; $C_2$-$C_{18}$alkenylene, $C_2$-$C_{18}$alkynylene, $C_2$-$C_{20}$alkylidene, $C_7$-$C_{20}$phenylalkylidene, $C_5$-$C_8$cycloalky $C_7$-$C_8$bicycloalkylene, unsubstituted or $C_1$-$C_4$alkyl-substituted phenylene or naphthylene;

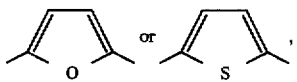

$R_{20}$ is $C_1$-$C_{18}$alkyl, unsubstituted or $C_1$-$C_4$alkyl-substituted $C_5$-$C_{12}$cycloalkyl; unsubstituted or $C_1$-$C_4$alkyl-substituted phenyl; $C_7$-$C_9$phenylalkyl or —$(CH_2)_rCOOR_{21}$.

$R_{21}$ is $C_1$-$C_{18}$ alkyl, unsubstituted or $C_1$-$C_4$alkyl-substituted $C_5$-$C_{12}$cycloalkyl; unsubstituted or $C_1$-$C_4$alkyl-substituted phenyl; or $C_7$-$C_9$phenylalkyl.

$R_{22}$ is $C_1$-$C_{25}$alkyl, unsubstituted or $C_1$-$C_4$alkyl-substituted phenyl; $C_7$-$C_9$phenylalkyl, $C_1$-$C_{25}$alkanoyl, $C_3$-$C_{25}$alkenoyl, $C_3$-$C_{25}$alkanoyl which is interrupted by oxygen, sulfur or >N—$R_5$; $C_6$-$C_9$cycloalkylcarbonyl, unsubstituted or $C_1$-$C_{12}$alkyl-substituted benzoyl; thenoyl or furoyl.

$R_{23}$ is $C_1$-$C_8$alkyl.

$R_{24}$ is a direct bond, $C_1$-$C_{18}$alkylene, $C_2$-$C_{18}$alkylene which is interrupted by oxygen, sulfur or >N—$R_5$; $C_2$-$C_{18}$alkenylene, $C_2$-$C_{20}$alkylidene, $C_7$-$C_{20}$phenylalkylidene, $C_5$-$C_8$-cycloalkylene, $C_7$-$C_8$bicycloalkylene, unsubstituted or $C_1$-$C_4$alkyl-substituted phenylene or naphthylene;

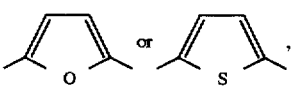

$R_{25}$ is $C_1$-$C_{18}$alkylene, $C_2$-$C_{18}$alkylene which is interrupted by oxygen, sulfur or >N—$R_5$; $C_2$-$C_{18}$alkenylene, $C_2$-$C_{20}$alkylidene, $C_7$-$C_{20}$phenylalkylidene, $C_5$-$C_8$cycloalkylene, $C_7$-$C_8$bicycloalkylene, unsubstituted or $C_1$-$C_4$alkyl-substituted phenylene or naphthylene;

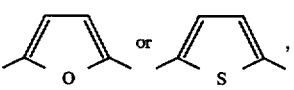

$R_{33}$ is hydrogen, $C_1$-$C_8$alkyl or a radical of formula XVII

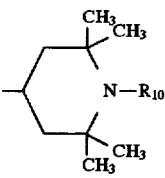
(XVII)

$R_{34}$ is hydrogen, $C_1$-$C_{20}$alkyl, $C_5$-$C_{12}$cycloalkyl, unsubstituted or $C_1$-$C_4$alkyl-substituted phenyl;

$R_{35}$ is $C_1$-$C_{25}$alkanoyl, unsubstituted or $C_1$-$C_4$alkyl-substituted benzoyl;

$X_3$ is oxygen or >N—$R_{33}$, $X_4$ is >C=O, >C=S or >CH—$R_{34}$, m is 0 or 1, n is an integer from 2 to 25, p is 0, 1 or 2, q is an integer from 3 to 8, and r is 1 or 2, with the proviso that in the structural repeating units of formula I the group L, the radial $R_1$, and the indices m are identical or different.

2. An oligmeric compound according to claim 1, wherein $R_1$ is $C_1$–$C_{18}$alkyl, $C_2$–$C_{18}$alkyl which is interrupted by oxygen; $C_2$–$C_{18}$alkenyl, $C_5$–$C_{15}$-cycloalkyl, $C_5$–$C_{15}$cycloalkenyl, $C_7$–$C_9$phenylalkyl or tetrahydroabietyl; or $R_1$ is a radical of formula IV

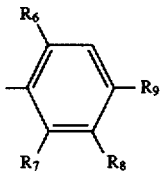

(IV)

$R_6$ and $R_7$ are each independently of the other hydrogen, $C_1$–$C_{18}$alkyl, $C_2$–$C_{18}$alkenyl, $C_5$–$C_8$cycloalkyl, phenyl, $C_5$–$C_8$cycloalkenyl, $C_7$–$C_9$phenylalkyl or —$CH_2$—S—$R_{20}$, $R_9$ is hydrogen, $C_1$–$C_{18}$alkyl, $C_2$–$C_{18}$alkenyl $C_5$–$C_8$cycloalkyl, phenyl, $C_5$–$C_8$cycloalkenyl, $C_7$–$C_9$phenylalkyl, —$CH_2$—S—$R_{20}$, —$(CH_2)_p COOR_{21}$ or —$(CH_2)_q OR_{22}$, $R_{20}$ is $C_1$–$C_{12}$alkyl, $C_5$–$C_{12}$cycloalkyl, phenyl, $C_7$–$C_9$phenylalkyl or —$(CH_2)_r COOR_{21}$, $R_{21}$ is $C_1$–$C_{12}$alkyl, $C_5$–$C_{12}$cycloalkyl, phenyl or $C_7$–$C_9$phenylaakyl, $R_{22}$ is $C_1$–$C_{18}$alkyl, phenyl, $C_7$–$C_9$phenylalkyl, $C_1$–$C_{18}$alkanoyl, $C_3$–$C_{18}$alkenoyl, $C_3$–$C_{18}$alkanoyl which is interrupted by oxygen; $C_6$–$C_9$cycloalkylcarbonyl, benzoyl, thenoyl or furoyl, and q is an integer from 3 to 6.

3. An oligomeric compound according to claim 1, wherein $R_1$ is $C_1$–$C_{12}$alkyl, $C_3$–$C_{12}$alkenyl, cyclohexyl, benzyl or tetrahydroabietyl, or $R_1$ is a radical of formula IV

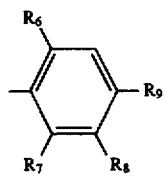

(IV)

$R_6$ and $R_7$ are each independently of the other hydrogen, $C_1$–$C_8$alkyl, cyclohexyl or phenyl, $R_9$ is hydrogen, $C_1$–$C_8$alkyl, cyclohexyl, phenyl or —$(CH_2)_p COOR_{21}$, $R_{21}$ is $C_1$–$C_{12}$alkyl or benzyl, n is an integer from 2 to 20, and p is 2.

4. An oligomeric compound according to claim 1, wherein $R_3$ is $C_1$–$C_{12}$alkylene, $C_2$–$C_{12}$alkylene which is interrupted by oxygen; $C_4$–$C_8$alkenylene or phenylethylene, $R_{11}$ is $C_1$–$C_8$alkyl,

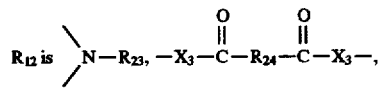

-continued

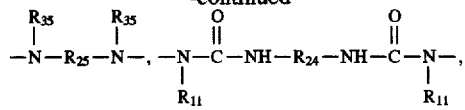

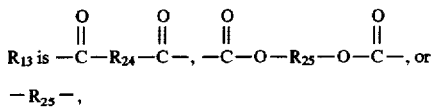

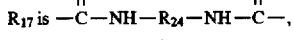

$R_{17}$ is $C_2$–$C_{12}$alkylene, $C_2$–$C_{12}$alkylene which is interrupted by oxygen; $C_2$–$C_{12}$alkenylene, $C_4$–$C_{12}$alkynylene, $C_2$–$C_{12}$alkylidene, $C_7$–$C_{12}$phenylalkylidene, $C_5$–$C_8$cycloalkylene or phenylene, $R_{24}$ is a direct bond, $C_1$–$C_{12}$alkylene, $C_2$–$C_{12}$alkylene which is interrupted by oxygen; $C_2$–$C_{12}$alkenylene, $C_2$–$C_{12}$alkylidene, $C_7$–$C_{12}$phenylalkylidene, $C_5C_8$cycloalkylene or phenylene, $R_{25}$ is $C_1$–$C_{12}$alkylene, $C_2$–$C_{12}$alkylene which is interrupted by oxygen; $C_2$–$C_{12}$alkenylene, $C_2$–$C_{12}$alkylidene, $C_7$–$C_{12}$phenylalkylidene, $C_5$–$C_8$cycloalkylene or phenylene, $R_{33}$ is hydrogen or $C_1$–$C_8$alkyl, $R_{34}$ is hydrogen, $C_1$–$C_{12}$alkyl, $C_5$–$C_{12}$cycloalkyl or phenyl, $X_4$ is >C=O or >CH—$R_{34}$, and n is an integer from 2 to 20.

5. An oligomeric compound according to claim 1, wherein $R_3$ is $C_1$–$C_8$alkylene, $C_2$–$C_8$alkylene which is interrupted by oxygen; or $C_4$–$C_8$alkenylene, $R_{11}$ is $C_1$–$C_6$alkyl,

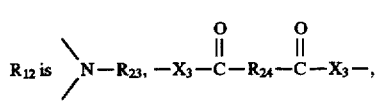

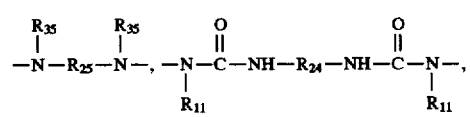

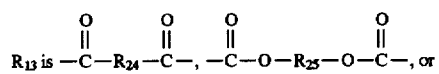

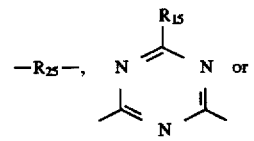

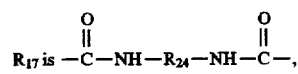

$R_{17}$ is $C_2$–$C_8$-alkylene, $C_4$–$C_{12}$alkynylene or $C_2$–$C_8$alkylidene, $R_{23}$ is $C_1$–$C_6$alkyl, $R_{24}$ is a direct bond, $C_1$–$C_{12}$alkylene, $C_2$–$C_{12}$alkylene which is interrupted by oxygen; $C_2$–$C_8$alkenylene or $C_2$–$C_8$alkylidene, $R_{25}$ is $C_2$-$C_{12}$alkylene, $C_2$-$C_{12}$alkylene which is interrupted by oxygen; $C_2$-$C_{12}$alkenylene or $C_2$-$C_{12}$alkylidene, $R_{33}$ is hydrogen or $C_1$-$C_8$alkyl, $R_{34}$ is hydrogen or $C_1$-$C_8$alkyl, $R_{35}$ is $C_1$-$Cl_2$alkanoyl, on benzoyl or $X_4$ is >C=O or >CH—$R_{34}$, and n is an integer from 2 to 15.

6. An oligomeric compound according to claim 1, wherein $R_1$ is a radical of formula IV

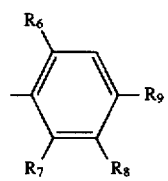   (IV)

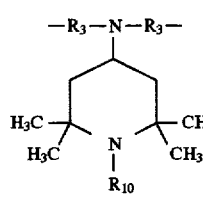   (V)

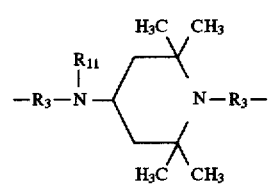   (VI)

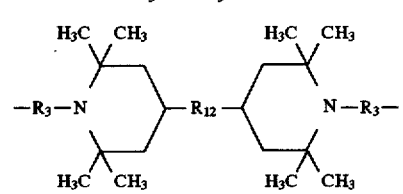   (VII)

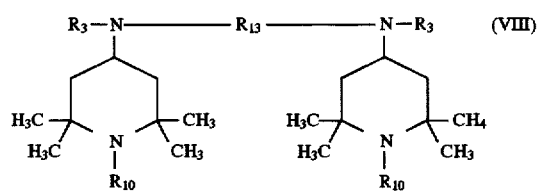   (VIII)

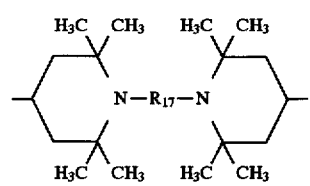   (XII)

$R_2$ is a group of formula V, VI, VII, VIII, XI, XII or XVI $R_3$ is methylene or ethylene, $R_4$ is $C_1$-$C_8$alkyl, $R_6$ and $R_7$ are each independently of the other hydrogen or $C_1$-$C_4$alkyl, $R_8$ is hydrogen, $R_9$ is hydrogen or $C_1$-$C_4$alkyl, $R_{10}$ is hydrogen or $C_1$-$C_4$alkyl, $R_{11}$ is $C_1$-$C_4$alkyl,

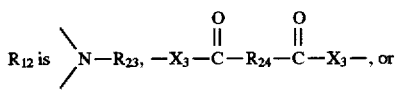

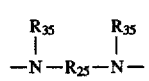

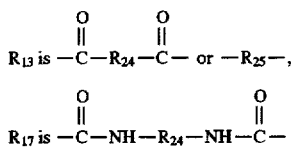

or $C_4$-$C_6$alkynylene, $R_{23}$ is $C_1$-$C_4$alkyl, $R_{24}$ is $C_2$-$C_8$alkylene, $R_{25}$ is $C_2$-$C_8$alkylene, $R_{26}$ is $C_1$-$C_4$alkyl, $R_{32}$ is hydrogen or $C_1$-$C_4$alkyl, $R_{33}$ is hydrogen or $C_1$-$C_4$alkyl, $R_{35}$ is $C_1$-$C_4$alkanoyl, $X_1$ is a group of formula XVIII $X_3$ is oxygen or >N—$R_{33}$, and n is an integer from 2 to 10.

7. A process for the preparation of an oligomeric compound of formula I according to claim 1, which comprises reacting a compound of formula XXII or a mixture of compounds of formula XXII

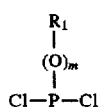   (XXII)

wherein the general symbols are as defined in claim 1, with a compound of formula XXIII or a mixture of compounds of formula XXIII

H—L—H   (XXIII)

wherein L is as defined in claim 1.

8. An oligomeric product obtainable by reacting a compound of formula XXII or a mixture of compounds of formula XXII with a compound of formula XXIII or a mixture of compounds of formula XXIII

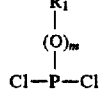   (XXII)

H—L—H   (XXIII)

wherein the general symbols are as defined in claim 1.

* * * * *